United States Patent
Kim et al.

(10) Patent No.: US 9,453,246 B2
(45) Date of Patent: Sep. 27, 2016

(54) YEAST CELL HAVING REDUCED ETHANOL PRODUCTIVITY AND USE OF THE YEAST CELL

(71) Applicant: Samsung Electronics Co., Ltd., Suwon-si, Gyeonggi-do (KR)

(72) Inventors: Sungsoo Kim, Hwaseong-si (KR); Changduk Kang, Gwacheon-si (KR); Kwangmyung Cho, Seongnam-si (KR); Seunghyun Lee, Asan-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/560,876

(22) Filed: Dec. 4, 2014

(65) Prior Publication Data

US 2015/0167031 A1    Jun. 18, 2015

(30) Foreign Application Priority Data

Dec. 4, 2013    (KR) .................. 10-2013-0149993

(51) Int. Cl.
| | |
|---|---|
| *C12N 1/00* | (2006.01) |
| *C12P 7/56* | (2006.01) |
| *C07H 21/04* | (2006.01) |
| *C12N 9/04* | (2006.01) |
| *C12N 9/88* | (2006.01) |

(52) U.S. Cl.
CPC .............. *C12P 7/56* (2013.01); *C12N 9/0006* (2013.01); *C12N 9/88* (2013.01); *C12Y 101/01001* (2013.01); *C12Y 101/01008* (2013.01); *C12Y 101/02004* (2013.01); *C12Y 401/01001* (2013.01); *Y02E 50/17* (2013.01)

(58) Field of Classification Search
None
See application file for complete search history.

(56) References Cited

U.S. PATENT DOCUMENTS

| | | |
|---|---|---|
| 7,622,284 B2 | 11/2009 | Op Den Camp et al. |
| 8,071,357 B2 | 12/2011 | Sawai et al. |
| 2005/0112737 A1 | 5/2005 | Liu et al. |
| 2010/0129883 A1 | 5/2010 | Eiteman et al. |
| 2011/0039316 A1 | 2/2011 | Onishi et al. |
| 2012/0129231 A1 | 5/2012 | Wang et al. |
| 2013/0023021 A1 | 1/2013 | Nilsson et al. |

FOREIGN PATENT DOCUMENTS

| | | |
|---|---|---|
| EP | 1 975 232 A1 | 10/2008 |
| EP | 2 147 976 A2 | 1/2010 |
| JP | 2006-006271 A | 1/2006 |
| JP | 2007-174947 A | 7/2007 |

OTHER PUBLICATIONS

Medina et al. Appl and Environ Microbiol, Jan. 2010, vol. 76(1):p. 190-195.*
Mazumdar et al. Appl and Environ Microbiol, Jul. 2010, vol. 76(13):p. 4327-4336.*
Nordling et al., Medium-chain dehydrogenases/reductases (MDR) Family characterizations including genome comparisons and active site modelling, *Eur.J. Biochem.*, 269: 4267-4276 (2002).

* cited by examiner

*Primary Examiner* — Iqbal H Chowdhury
(74) *Attorney, Agent, or Firm* — Leydig, Voit & Mayer, Ltd.

(57) ABSTRACT

A yeast cell, in which an alcohol dehydrogenase 6 activity is increased and an activity of converting acetaldehyde to ethanol is decreased, a method of decreasing ethanol production by using the yeast cell, and a method of producing lactate.

18 Claims, 7 Drawing Sheets

YEAST CELL HAVING REDUCED ETHANOL PRODUCTIVITY AND USE OF THE YEAST CELL

CROSS-REFERENCE TO RELATED APPLICATIONS

This application claims the benefit of Korean Patent Application No. 10-2013-0149993, filed on Dec. 4, 2013, in the Korean Intellectual Property Office, the disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: One 35,992 Byte ASCII (Text) file named "716722_ST25.TXT-Revised" created on Feb. 19, 2015.

BACKGROUND

1. Field

The present disclosure relates to a yeast cell having decreased ethanol productivity and a use of the yeast cell.

2. Description of the Related Art

Lactate is an organic acid that is broadly used in various industrial fields, such as food, pharmaceutics, chemicals, and electronics. Lactate is colorless, odorless, and a low-volatile material that dissolves well in water. Lactate is non-toxic to the human body and thus may be used as a flavor agent, a taste agent, or a preserving agent. Also, lactate is an environment-friendly alternative polymer material and a raw material of a polylactic acid (PLA) that is biodegradable plastic.

PLA is a polyester-based resin that is ring-open polymerized by converting it into lactide, which is a dimer, for technical polymerization and may be variously processed into a film, sheet, fiber, plastic, etc. Thus, demands for PLA as bioplastic have recently increased to broadly replace conventional typical petrochemical plastic, such as polyethylene (PE), polypropylene (PP), polyethylene terephthalate (PET), or polystyrene (PS).

In addition, lactate includes both a hydroxyl group and a carboxyl group and thus is highly reactive. Accordingly, lactate is easily converted into an industrially important compound, such as lactate ester, acetaldehyde, or propyleneglycol, and thus has received attention as an alternative chemical material of the next generation in chemical industry.

Currently, lactate is produced by an industrially petrochemical synthesis process and a biotechnological fermentation process. The petrochemical synthesis process is performed by oxidizing ethylene derived from crude oil, preparing lactonitrile through addition of hydrogen cyanide after acetaldehyde, purifying by distillation, and hydrolyzing by using chloric acid or phosphoric acid. Also, the biotechnological fermentation process is used to manufacture lactate from a reproducible carbon hydrate, such as, starch, sucrose, maltose, glucose, fructose, or xylose, as a substrate.

Therefore, a cell strain for efficiently producing lactate and a lactate production method using the strain are needed.

SUMMARY

Provided is a yeast cell having reduced ethanol productivity.

Provided is a method of decreasing ethanol production by using the yeast cell.

Provided is a method of producing lactate by using the yeast cell.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
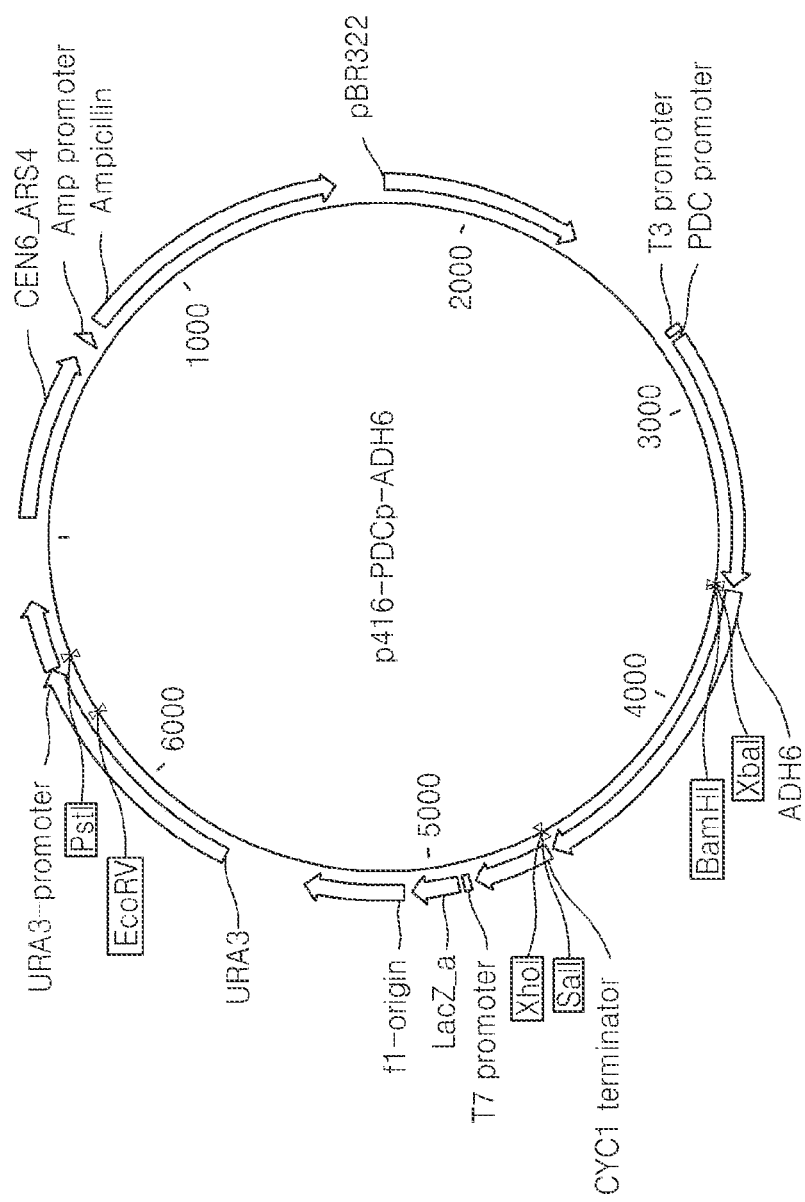
FIG. 1 is a schematic of a p416-PDCp-ADH6 vector.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

According to an embodiment of the present invention, a yeast cell is provided, wherein the yeast cell has an increased activity of alcohol dehydrogenase 6 (i.e., increased alcohol dehydrogenase 6 activity) and a depressed (i.e., decreased) activity for converting acetaldehyde to alcohol.

According to an embodiment of the present invention, a yeast cell is provided, wherein the yeast cell includes a gene that encodes alcohol dehydrogenase 6 and a depressed activity for converting acetaldehyde to ethanol.

As used herein, the term "lactate" refers to "a lactic acid" or a salt thereof.

As used herein, the term "activity increase", "enzyme activity increase", "increased activity", or "increased enzyme activity" denotes that a cell or an isolated enzyme has an increased activity level compared to an activity level of a comparable parent cell or wild-type enzyme. That is, an enzyme conversion activity from a substrate to a product with respect to a corresponding enzyme may be at least about 5%, at least about 10%, at least about 15%, at least about 20%, at least about 30%, at least about 50%, at least about 60%, at least about 70%, or at least about 100% increased compared to the same biochemical conversion activity of a parent cell or wild-type enzyme. A cell having an increased enzyme activity of an enzyme may be confirmed by using any method commonly known in the art.

The term "parent cell" denotes a cell not having a specific genetic modification resulting in a genetically engineered cell. The parent cell also denotes a cell to which is not applied a genetic modification of interest gene for identifying biochemical and/or genetic function of the interest gene. The parent cell also may refer to an original cell, for example, a non-engineered cell of the same type as an engineered yeast cell. With respect to a particular genetic modification, the "parent cell" can be a cell that lacks the particular genetic modification, but is identical in all other respects. Thus, a parent cell can be a cell used as starting material to produce a genetically engineered yeast cell having an activated or increased activity of a given protein (e.g., a protein having a sequence identity of about 95% or more to an alcohol dehydrogenase 6). The term "wild-type" enzyme, polypeptide or polynucleotide denotes an enzyme, a polypeptide or a polynucleotide not having a specific genetic modification resulting in a genetically engineered enzyme, polypeptide or polynucleotide.

The increased activity of the enzyme or polypeptide may occur due to an increased expression or an increased specific activity. The increased expression may occur by introducing a polynucleotide encoding a polypeptide into a cell repetitively, or mutating a coding region of the polynucleotide. A polynucleotide that is introduced or present in an increased copy number may be an endogenous gene or an exogenous gene. The endogenous gene refers to a gene that exists in a genetic material included in a microorganism. The exogenous gene refers to a gene that is introduced into a host cell, such as a gene that is integrated into a host cell genome, wherein the introduced gene may be homologous or heterologous with respect to the host cell genome.

The expression "increased copy number" may include a copy number increase by an introduction or amplification of the gene. The expression "increased copy number" may also include a copy number increase by genetically manipulating a cell that does not have a gene so as to have the gene in the cell. The introduction of the gene may occur by using a vehicle such as a vector. The introduction may be a transient introduction, in which the gene is not integrated into the genome, or an integration into the genome. The introduction may, for example, occur by introducing a vector inserted with a polynucleotide encoding a desired polypeptide into the cell and then replicating the vector in the cell or integrating the polynucleotide into the genome of the cell and then replicating the polynucleotide together with the replication of the genome.

Meanwhile, as used herein, an "inactivated" "depressed" or "reduced" activity of an enzyme or a polypeptide, or an enzyme having an activity that is "inactivated" or "reduced" denotes a cell, an isolated enzyme, or a polypeptide having an activity that is lower than an activity measured in a cell of the comparably same type or the original enzyme or having no activity. That is, an enzyme conversion activity from a substrate to a product with respect to a corresponding enzyme may be about 20% or more, about 30% or more, about 40% or more, about 50% or more, about 55% or more, about 60% or more, about 70% or more, about 75% or more, about 80% or more, about 85% or more, about 90% or more, about 95% or more, or about 100% reduced than the biochemical conversion activity by an enzyme that is not originally controlled. The cells having reduced activity of the enzyme may be confirmed by using a commonly known method in the art. The inactivation or reduction includes the case when a gene-encoding enzyme is not expressed or has a less amount of expression compared to the gene that is not originally controlled even when the enzyme is expressed or when an activity of the enzyme is removed or reduced.

An activity of the enzyme may be inactivated or reduced due to substitution, addition, or deletion of a part or a whole gene encoding the enzyme. For example, inactivation or reduction of the enzyme may be caused by homologous recombination or may be performed by transforming a vector including a part of sequence of the gene to the cell, culturing the cell so that the sequence may homogonously recombined with an endogenous gene of the cell, and then selecting cells, in which homologous recombination occurred, using a selection marker.

As used herein, the term "gene" refers to a nucleic acid segment expressing a specific protein, and the gene may or may not include a regulatory sequence of a 5'-non coding sequence and a 3'-non coding sequence.

As used herein, the term "inactivation" may refer to generating a gene that is not expressed at all or a gene that has no activity even when it is expressed. The term "depression" may refer to generating a gene whose expression level is reduced lower than those of a parent yeast cell, or a gene which encodes a protein with decreased activity although it is expressed. The inactivation or depression may be due to mutation, substitution, or deletion of a part of or the whole gene or insertion of at least one base group to a gene. The inactivation or depression may be achieved by gene manipulation such as homogenous recombination, mutation generation, or molecule evolution. When a cell includes a plurality of the same genes or at least two different polypeptide paralogous genes, one or more genes may be inactivated or depressed. The inactivation or depression may be performed by transforming a vector including some sequences of the gene to a cell, and allow the sequences to be homogeneously recombined with an endogenous gene by culturing the cell, and then by selecting the homogenously recombined cell by using a selection marker.

An increase in an enzyme activity refers to an increase in an expression level such as an overexpression of a gene encoding an enzyme having the activity or an increase in non-activity of the enzyme itself compared to a cell not having a specific genetic modification resulting in a genetically engineered cell.

As used herein, the term "sequence identity" of a nucleic acid or a polypeptide refers to a degree of similarity of base groups or amino acid residues between two aligned sequences, when the two sequences are aligned to match each other to the greatest extent possible, at corresponding positions. The sequence identity is a value that is measured by aligning to an optimum state and comparing the two sequences at a particular comparing region, wherein a part of the sequence within the particular comparing region may be added or deleted compared to a reference sequence. A sequence identity percentage may be calculated, for example, by 1) comparing the two sequences aligned within the whole comparing region to an optimum 2) obtaining the number of matched locations by determining the number of locations represented by the same amino acids of nucleic acids in both of the sequences, 3) dividing the number of the matched locations by the total number of the locations within the comparing region (i.e., a range size), and 4) obtaining a percentage of the sequence identity by multiplying 100 to the result. The sequence identity percent may be determined by using a common sequence comparing program, for example, BLASTN(NCBI), CLC Main Workbench (CLC bio), MegAlign™ (DNASTAR Inc).

In confirming many different polypeptides or polynucleotides having the same or similar function or activity, sequence identities at several levels may be used. For example, the sequence identities may be about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, or 100%.

The yeast cell may have depressed ethanol productivity. The yeast cell may have about 5% or more, about 10% or more, about 15% or more, about 25% or more, about 30% or more, about 35% or more, about 40% or more, about 50% or more, about 60% or more, or about 65% or more depressed polypeptide activity capable of converting acetaldehyde to ethanol.

The yeast cell may be ascomycota. The ascomycota may be saccharomycetacease. The saccharomycetaceae may be *Saccharomyces* genus, *Kluyveromyces* genus, *Candida* genus, *Pichia* genus, *Issatchenkia* genus, *Debaryomyces* genus, *Zygosaccharomyces* genus, *Shizosaccharomyces* genus, or *Saccharomycopsis* genus. The *Saccharomyces* genus may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum,* or *S. zonatus*. The *Kluyveromyces* genus may be *Kluyveromyces lactis, Kluyveromyces marxianus,* or *Kluyveromyces thermotolerans*. The *Candida* genus may be *Candida glabrata, Candida boidinii, Candida magnolia, Candida methanosorbosa, Candida sonorensis,* or *Candida utilis*. The *Pichia* genus may be *Pichia stipitis*. The *Issatchenkia* genus may be *Issatchenkia orientalis*. The *Debaryomyces* genus may be *Debaryomyces hansenii*. The *Zygosaccharomyces* genus may be *Zygosaccharomyces bailli* or *Zygosaccharomyces rouxii*. The *Shizosaccharomyces* genus may be *S. cryophilus, S. japonicus, S. octosporus,* or *S. pombe*.

The yeast cell may include a mutant yeast cell for producing a desired production, such as lactate, as well as a natural yeast cell. The mutant yeast cell may have resistance with respect to, for example, uracil, sulfurguanidine, sulfathiazole, azaserine, trimethoprim, or monofluoroacetate.

The alcohol dehydrogenase 6 is an enzyme that belongs to a medium-chain dehydrogenase/reductase (MDR) and belongs to a cinnamyl alcohol dehyrogenase (CAD) family. Unlike other alcohol dehydrogenases of yeast, the alcohol dehydrogenase 6 has a specificity that is strong with respect to NADPH and may have a Km value of, for example, about 0.029 mM. Also, the alcohol dehydrogenase 6 may have an activity with respect to a wide range of aliphatic or aromatic aldehydes, for example, pentanal, veratraldehyde, and furfural. When the activity of the alcohol dehydrogenase 6 in a yeast cell is increased, an excessive amount of NADPH, which is a cofactor, is oxidized to $NADP^+$ and thus may affect redox balance in the cell.

The depressed activity of converting acetaldehyde to ethanol may be caused by a decreased expression of alcohol dehydrogenase 1 converting acetaldehyde to ethanol. The alcohol dehydrogenase 1 may be an enzyme that catalyzes reversible conversion of acetaldehyde to ethanol by using oxidation of NADH to $NAD^+$. The alcohol dehydrogenase may belong to EC 1.1.1.1.

Due to the introduction of a gene encoding the enzyme having a small Km value compared to a Km value with respect to NADH of the alcohol dehydrogenase, carbon flux may be shifted by the introduced enzyme, and thus an activity of the enzyme may increase. In this regard, due to the increased activity of the enzyme, an amount of the production generated by expression of the enzyme may increase. For example, the enzyme having a small Km value compared to a Km value with respect to NADH of the alcohol dehydrogenase may be a lactate dehydrogenase converting pyruvate to lactate.

In the yeast cell, the alcohol dehydrogenase 6 activity may increase due to increased expression, for example, overexpression of the alcohol dehydrogenase 6 (ADH6). The Adh6p may include an amino acid sequence having about 50% or more, about 70% or more, about 80% or more, about 90% or more, about 95% or more, about 96% or more, about 97% or more, about 98% or more, about 99% or more, or about 100% or more of a sequence identity with an amino acid sequence of SEQ ID NO: 1. The alcohol dehydrogenase 6 activity may be provided by introduction of the gene encoding Adh 6. The gene encoding Adh 6 may have a nucleotide sequence of SEQ ID NO: 2.

In the yeast cell, an activity of polypeptide capable of converting pyruvate to acetaldehyde may be further removed or depressed. The term "depressed" may refer to an activity of the genetically engineered yeast cell that is reduced when compared to that of a yeast cell of the same type (e.g., same species) that is a parent yeast cell.

In the yeast cell, a gene encoding a polypeptide capable of converting pyruvate to acetaldehyde may be inactivated or depressed.

The activity may refer to about 50% or more, about 55% or more, about 60% or more, about 70% or more, about 75% or more, about 80% or more, about 85% or more, about 90% or more, about 95% or more, or about 100% or more reduced activity of a polypeptide capable of converting pyruvate to acetaldehyde compared to an activity of an appropriate control group.

The inactivation or depression may be achieved by transforming a vector including some sequences of the gene to a cell, culturing the cell to allow the sequences to be homogeneously recombined with an endogenous gene, and then selecting the homogenously recombined cell by using a selection marker. The selection marker may provide resistance against drug, nutritional requirement, resistance against a cytotoxic agent, or selectable expression, such as surface protein expression.

The polypeptide capable of converting pyruvate to acetaldehyde may be a pyruvate decarboxylase or an enzyme that belongs to EC 4.1.1.1. The polypeptide converting pyruvate to acetaldehyde may include an amino acid sequence having about 50% or more, about 70% or more, about 80% or more, about 90% or more, about 95% or more, about 96% or more, about 97% or more, about 98% or more, about 99% or more, or about 100% or more sequence identity with an amino acid sequence SEQ ID NO: 3. The gene encoding the polypeptide capable of converting pyruvate to acetaldehyde may include a nucleotide sequence SEQ ID NO: 4. The gene may be PDC1 or PDC2 that encodes a pyruvate decarboxylase (Pdc).

Also, in the yeast cell, an activity of a polypeptide capable of converting lactate to pyruvate, an activity of a polypeptide converting DHAP to glycerol-3-phosphate, or a combination thereof may be removed or decreased.

The yeast cell may have an inactivated or depressed gene that encodes a polypeptide capable of converting lactate to pyruvate. The polypeptide capable of converting lactate to pyruvate may be a cytochrome c-dependent enzyme. The polypeptide capable of converting lactate to pyruvate may be a lactate cytochrome-c oxydoreductase (Cyb2). The lactate cytochrome c-oxydoreductase may be an enzyme that belongs to EC 1.1.2.4 acting on D-lactate or EC 1.1.2.3 acting on L-lactate. The polypeptide capable of converting lactate to pyruvate may include an amino acid sequence having about 50% or more, about 70% or more, about 80% or more, about 90% or more, about 95% or more, about 96% or more, about 97% or more, about 98% or more, about 99% or more, or about 100% or more sequence identity with an amino acid sequence of SEQ ID NO: 5. The gene that encodes the polypeptide capable of converting lactate to pyruvate may have a nucleotide sequence of SEQ ID NO: 6.

In the yeast cell, the gene that encodes a polypeptide capable of converting DHAP to glycerol-3-phosphate may be inactivated or depressed. The polypeptide capable of converting DHAP to glycerol-phosphate may be an enzyme catalyzing reduction of DHAP to glycerol-3-phosphate by using oxidation of NADH to $NAD^+$. The enzyme may belong to EC 1.1.1.8. The polypeptide may be cytosolic glycerol-3-phosphate dehydrogenase (Gpd1). The polypeptide capable of converting DHAP to glycerol-3-phosphate may include an amino acid sequence having about 50% or more, about 70% or more, about 80% or more, about 90% or more, about 95% or more, about 96% or more, about 97% or more, about 98% or more, about 99% or more, or about 100% or more sequence identity with an amino acid sequence SEQ ID NO: 7. The gene that encodes the polypeptide capable of converting DHAP to glycerol-3-phosphate may have a nucleotide sequence of SEQ ID NO: 8. The gene may be gdp1 that encodes a glycerol-3-phosphate dehydrogenase.

In the yeast cell, the activity for converting pyruvate to lactate may increase. The yeast cell may have a lactate-producing ability. The activity may be increased sufficiently enough to produce lactate. The activity may be about 5% or more, about 10% or more, about 15% or more, about 20% or more, about 30% or more, about 50% or more, about 60% or more, about 70% or more, or about 100% or more increased compared to an activity of a control group. Due to the introduction of a gene encoding a lactate dehydrogenase that converts pyruvate to lactate and has a small Km value compared to a Km value with respect to NADH of the alcohol dehydrogenase, carbon flux may be shifted by the lactate dehydrogenase, and thus the lactate dehydrogenase activity may increase. In this regard, due to the increased lactate dehydrogenase activity, an amount of lactate production generated by increased activity of the lactate dehydrogenase may increase.

A polynucleotide encoding a lactate dehydrogenase (hereinafter referred to as "LDH") may be an enzyme that catalyzes conversion of pyruvate to lactate. The lactate dehydrogenase may be a NAD(P)-dependent enzyme, acting on L-lactate or D-lactate. The NAD(P)-dependent enzyme may be an enzyme that belongs to EC 1.1.1.27 acting on L-lactate or EC 1.1.1.28 acting on D-lactate. The lactate dehydrogenase may have an amino acid sequence having about 50% or more, about 70% or more, about 80% or more, about 90% or more, about 95% or more, about 96% or more, about 97% or more, about 98% or more, about 99% or more, or about 100% or more sequence identity with an amino acid sequence of SEQ ID NO: 14. A gene encoding the lactate dehydrogenase may have a nucleotide sequence of SEQ ID NO: 15. In the yeast cell, the lactate dehydrogenase activity converting pyruvate to lactate may be increased due to an increased expression of lactate dehydrogenase converting pyruvate to lactate.

The increased expression may be caused by introduction of a gene encoding a lactate dehydrogenase. The gene may be an exogenous gene. The exogenous gene may be homologous or heterologous. The exogenous gene that encodes a lactate dehydrogenase may be introduced at a downstream position of a promoter enabling expression of a gene that encodes a lactate dehydrogenase. Also, a polynucleotide that encodes a lactate dehydrogenase (also, referred to as "LDH") may be included in a genome of a yeast cell. When a polynucleotide encoding LDH functions for production of active proteins in a cell, the polynucleotide is considered "functional" in a cell. A yeast cell including the polynucleotide encoding L-LDH or D-LDH may produce a L-lactate enantiomer, a D-lactate enantiomer, or a salt thereof. The copy number of the gene encoding LDH may increase due to the introduced gene that encodes LDH.

The yeast cell may include a gene that encodes one lactate dehydrogenase or multiple genes that encode 1 to 10 copies of lactate dehydrogenase. The multiple genes may encode, for example, 1 to 8, 1 to 5, 1 to 4, or 1 to 3 copies of lactate dehydrogenase. When the yeast cell includes the genes encoding multiple copies of lactate dehydrogenase, each of the genes may be a copy of the same gene or may include a copy of a gene that encodes at least two different lactate dehydrogenases. Multiple copies of a gene encoding exogenous lactate dehydrogenase may be included in the same locus or in multiple loci within a host cell's genome. The exogenous lactate dehydrogenase may have a better activity than an endogenous lactate dehydrogenase of a yeast cell.

The polynucleotide encoding LDH may be derived from bacteria, yeast, fungi, mammals, or reptiles. The fungi may include *Sordaria* genus. The *Sordaria* genus may be *Sordaria macrospora*, *Sordaria fimicola*, *Sordaria alcina*, *Sordaria araneosa*, *Sordaria brevicollis*, *Sordaria equina*, *Sordaria heterothallis*, *Sordaria humana*, *Sordaria lappae*, *Sordaria sclerogenia*, *Sordaria superba*, or *Sordaria tomento-alba*. The *Sordaria* genus may be *Sordaria macrospora*.

Also, the increase in expression may be caused by mutation of a regulation region of the gene encoding LDH. Also, the increased LDH activity may be due to modification of the LDH caused by its mutation.

The yeast cell may further include a polynucleotide encoding LDH which may be a vector including LDH derived from bacteria, yeast, fungi, mammals, or reptiles. The vector may include a replication initiation point, a promoter, a polynucleotide encoding LDH, and a terminator. The replication initiation point may include a yeast autonomous replication sequence (ARS). The yeast ARS may be stabilized by a yeast centrometric sequence (CEN). The promoter may be selected from the group consisting of a CYC promoter, a TEF promoter, a GPD promoter, and an ADH promoter. The CYC promoter, TEF promoter, GPD promoter, and ADH promoter may, each respectively, have nucleotide sequences of SEQ ID NOS: 9, 10, 11, and 12. The terminator may be selected from the group consisting of phosphoglycerate kinase 1 (PGK1), cytochrome c transcription (CYC1), and GAL1. The CYC1 terminator may have a nucleotide sequence of SEQ ID NO: 13. The vector may further include a selection marker.

In the yeast cell, an activity of alcohol dehydrogenase 6 may be increased and an activity for converting acetaldehyde to ethanol may be depressed. In one embodiment of the yeast cell, a gene encoding alcohol dehydrogenase 6 is inserted; a gene encoding a polypeptide that converts pyruvate to acetaldehyde, the gene encoding a polypeptide that converts lactate to pyruvate, the gene encoding a polypeptide that converts DHAP to glycerol-3-phsophate, or a combination thereof is inactivated or depressed, and a gene encoding a polypeptide that converts pyruvate to lactate may be inserted. The yeast cell may produce lactate at an increased percent yield of at least about 20% to about 50%, about 25% to about 45%, about 26% to about 40%, about 27% to about 35%, or about 28% to about 30% compared to a percent yield of a mother cell having an alcohol dehydrogenase 6 activity that is not increased. Also, the cell may produce lactate at a percent yield of about 40% to about 55%, for example, about 45% to about 50%, about 46% to about 50%, about 47% to about 50%, about 48% to about 50%, or about 49% to about 50%, which is a ratio of produced lactate to consumed glucose.

An expression vector including the polynucleotide encoding alcohol dehydrogenase 6 is provided to prepare a yeast cell including a gene that has an increased alcohol dehydrogenase 6 activity or a gene that encodes alcohol dehydrogenase 6, wherein an activity of converting acetaldehyde to ethanol is reduced in the yeast cell.

The polynucleotide may be operably linked to a regulation sequence appropriate for expressing the polynucleotide in an appropriate host. The regulation sequence may include a promoter, a terminator, or an enhancer. Also, the promoter may be operably linked with a sequence encoding a gene. As used here, the term "operably linked" denotes a functional connection between a nucleic acid expression-regulation sequence and another nucleotide sequence. In this regard, the regulation sequence may control transcription and/or translation of a nucleotide sequence encoding the gene.

The yeast expression vector may be, for example, a vector for expression in *Saccharomyces cerevisiae*, and examples of the yeast expression vector may include pYepSec1, 2i, pAG-1, Yep6, Yep13, PEMBLYe23, pMFa, pJRY88, and pYES2.

In order to serve as an expression vector, the vector may include a replication origin, a promoter, a multiple cloning site (MCS), and a selection marker. The replication origin serves to allow a plasmid to have a replicating function independent from chromosomal replication in a host cell, the promoter works on the transcription process of an exogenous gene being inserted, the MCS allows the exogenous gene to be inserted through various restriction enzyme sites, and the selection marker serves to confirm whether the vector is properly introduced to the host cell. The selection marker may include an antibiotic-resistant gene, for example, a gene that is resistant to ampicillin, gentamicin, carbenicillin, chloramphenicol, streptomycin, kanamycin, geneticin, neomycin, or tetracycline. Also, the selection marker includes an auxotrophic gene and may include, for example, a gene providing auxotrophy to one selected from uracil, tryptophan, leucine, and histidine.

According to another aspect of the present invention, a method of decreasing an ethanol production, the method including culturing the yeast cell, is provided.

In the yeast cell, an alcohol dehydrogenase 6 activity may be increased. A gene encoding alcohol dehydrogenase 6 may be introduced to the yeast cell. The description of the yeast cell is as defined above.

The culturing may be performed in a carbon source, for example, a medium containing glucose. The medium used in the culturing of a yeast cell may be a common medium suitable for growth of a host cell such as a minimal or composite medium containing appropriate supplements. A suitable medium may be purchased from commercial suppliers or may be prepared according to a known preparation method.

The medium used in the culturing may be a medium that satisfies particular conditions for growing a yeast cell. The medium may be one selected from the group consisting of a carbon source, a nitrogen source, a salt, trace elements, and a combination thereof. A pH of a fermented solution may be controlled to be maintained in a range of about 2 to about 7.

The culturing of the yeast cell may be a continuous type, a semi-continuous type, a batch type, or a combination thereof.

The culturing condition for obtaining lactate from the genetically engineered yeast cell may be appropriately controlled. The culturing may be performed in an aerobic or anaerobic condition. For example, the yeast cell is cultured under an aerobic condition for its proliferation, and then, the yeast cell is cultured under an anaerobic condition to produce lactate. The anaerobic condition may include a microaerobic concentration having a dissolved oxygen (DO) concentration of 0% to 10%, for example, 0% to 8%, 0% to 6%, 0% to 4° A, or 0% to 2%.

The term "culture condition" indicates a condition for culturing a yeast cell. Such culture condition may be, for example, a carbon source, a nitrogen source, or an oxygen condition for the yeast cell to use. The carbon source used by the yeast cell includes monosaccharides, disaccharides, or polysaccharides. In particular, the carbon source may be glucose, fructose, mannose, or galactose. The nitrogen source used by the yeast cell may include an organic nitrogen compound or an inorganic nitrogen compound. In particular, the nitrogen source may be an amino acid, amide, amine, a nitrate, or an ammonium salt. The oxygen condition for culturing the yeast cell includes an aerobic condition of a normal oxygen partial pressure, a low-oxygen condition including 0.1% to 10% of oxygen in the atmosphere, or an anaerobic condition without oxygen. A metabolic pathway may be modified in accordance with the carbon source or the nitrogen source that may be practically used by the yeast cell.

According to another aspect of the present invention, provided is a method of producing lactate, the method including culturing the yeast cell in a cell culture medium, whereby the yeast cell produces lactate; and collecting lactate from the culture, is provided. The culturing process is as described above.

The obtaining of the lactate from the culture may be performed by separating the lactate from the culture by using a method commonly known in the art. The separation method may be centrifuge, filtration, ion-exchange chromatography, or crystallization. For example, the culture may be centrifuged at a low rate to remove a biomass, and the supernatant resulting therefrom may be separated through ion-exchange chromatography.

The present invention will be described in further detail with reference to the following examples. These examples are for illustrative purposes only and are not intended to limit the scope of the present invention.

Example 1

Preparation of ADH6 Overexpression Vector

A cassette for overexpressing ADH6 gene (SEQ ID NO: 2) encoding one of alcohol dehydrogenases (Adhs) was prepared as follows. First, PCR was performed with a genomic DNA of *Saccharomyces cerevisiae* as a template and using primers of SEQ ID NO: 16 and SEQ ID NO: 17, and the PCR fragment thus obtained was digested with SacI and XbaI, introduced to p416-GPD (ATCC® 87360™), producing p416-PDCp.

Then, PCR was performed with a genomic DNA of *Saccharomyces cerevisiae* as a template and using primers of SEQ ID NO: 18 and SEQ ID NO: 19, and the obtained ADH6 PCR fragment thus obtained and the prepared p416-PDCp were digested with XbaI and XhoI, ligated with the ADH6 PCR fragment to prepare p416-PDCp-ADH6. FIG. 1 is a schematic view of a p416-PDCp-ADH6 vector. The p416-PDCp-ADH6 vector is used as a template in preparation of a cassette for overexpressing ADH6.

Example 2

Introduction of ADH6 Overexpression Vector to Wild-Type *Saccharomyces cerevisiae*

In order to insert a p416-PDCp-ADH6 plasmid prepared in Example 1 to *Saccharomyces cerevisiae* CEN.PK2-1D (genotype: MATα ura3-52; trp1-289; leu2-3,112; his3Δ1; MAL2-8$^c$; SUC2, EUROSCARF accession number: 30000B), a process was performed as follows. The plasmid prepared in Example 1 was mixed with 50% polyethylene glycol and a single stranded carrier DNA and reacted in a water tub for about 1 hour at 42° C., and then, the culture solution was spread on a uracil-free minimal agar plate (including YSD, 6.7 g/L of yeast nitrogen base without amino acids, and 1.4 g/L of amino acid dropout mix (-ura)) and grown for about 24 hours or more at 30° C. Eight colonies (mutant strains) grown on the plate were selected, patched onto the fresh uracil-free minimal agar plate, and at the same time, inoculated into a YSD (-ura) liquid medium including the same components contained in the uracil-free minimal agar plate to isolate a plasmid DNA from the above mutant strains by using a commonly used kit (Yeast plasmid isolation kit, Clontech). In order to confirm the plasmid including ADH6, PCR was performed using the isolated plasmid DNA as a template with primers of SEQ ID NOS: 20 and 21, and then, electrophoresis was performed on the obtained PCR product to confirm that the inserted plasmid was p416-PDCp-ADH6. As a result, the strain was named CEN.PK2-1D(ADH6).

Example 3

Preparation of PDC1-Deleted *Saccharomyces cerevisiae* Strain and Preparation of PDC1-Deleted and ADH6-Overexpressed *Saccharomyces cerevisiae* Strain (3.1) Preparation of PDC1 Gene Deletion Cassette A gene deletion vector is prepared as follows to delete pyruvate decarboxylase 1 (PDC1) that is involved in production of ethanol from pyruvate by homogenous recombination.

In order to use an antibiotic marker, PCR was performed with a genomic DNA of *Saccharomyces cerevisiae* CEN.PK2-1D as a template and using primers of SEQ ID NO: 22 and SEQ ID NO: 23, and the resulting Gal10 terminator (Gal10t) PCR fragment was digested with NotI and inserted to pGEM-5Zf (Promega USA), producing pGEM-Gal10t.

Figure 2:
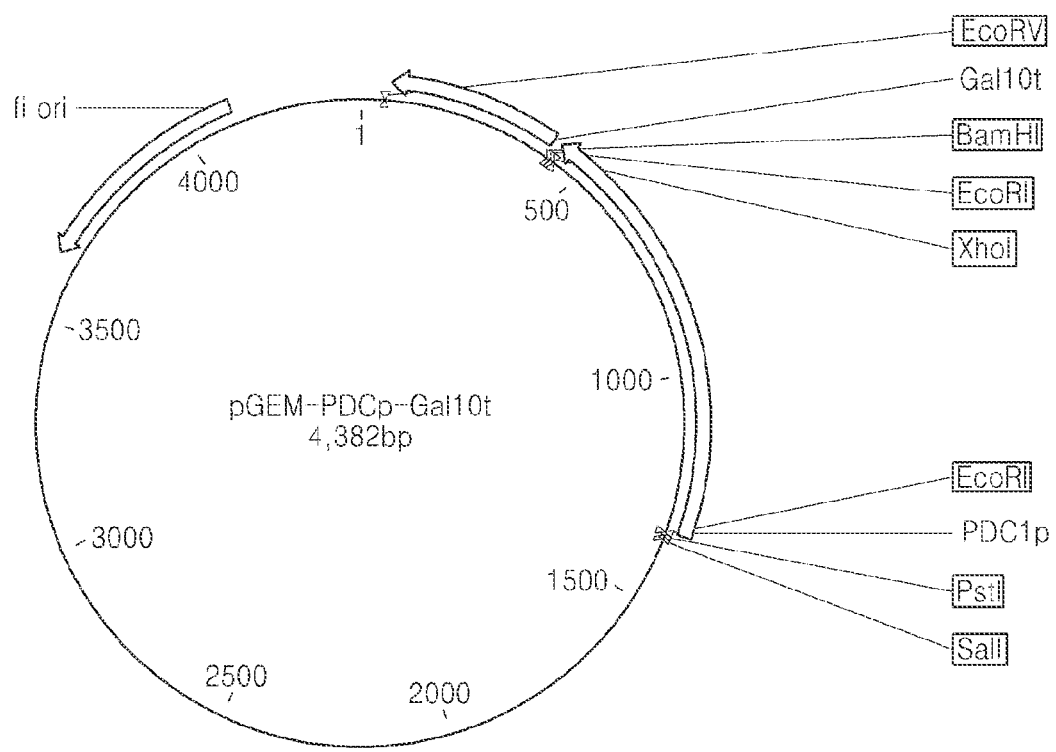
FIG. 2 is a schematic of a pGEM-PDCp-Gal10t vector.

Also, PCR was performed on a PDC promoter (PDCp) with a genomic DNA of *S. cerevisiae*, CEN.PK2-1D as a template and using primers of SEQ ID NO: 24 and SEQ ID NO: 25, and the resulting PCR fragment was digested with EcoRI, ligated to the pGEM-Gal10t that is digested with the same EcoRI, producing pGEM-PDCp-Gal10t. FIG. 2 is a schematic view of a pGEM-PDCp-Gal10t vector. A geneticin antibiotic resistive gene, NPT was inserted, and thus a pGEM-PDCp-Gal10t vector for overexpression was prepared.

Figure 3:
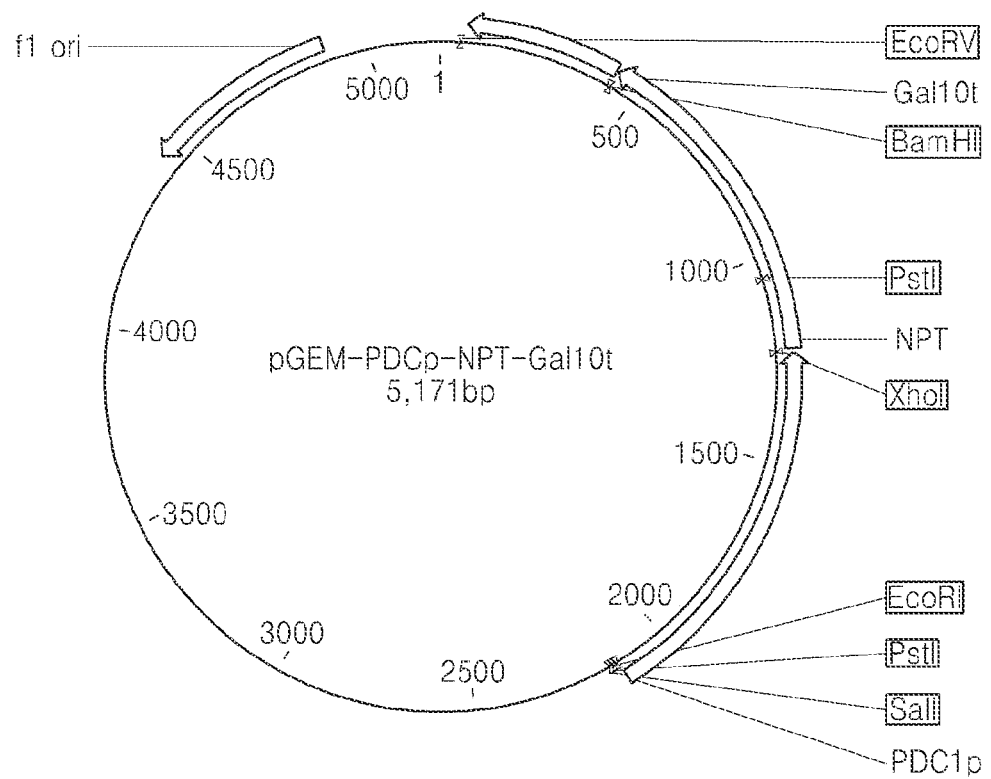
FIG. 3 is a schematic of a pGEM-PDCp-NPT-Gal10t vector, wherein the pGEM-PDCp-NPT-Gal10t vector is an NPT overexpression deletion vector, which is a template used to prepare a cassette for deleting PDC1.

Then, a neomycin phosphotransferase (NPT) gene capable of giving resistance to a geneticin (G418) antibiotic was obtained by performing PCR with pcDNA3.3-TOPO (Invitrogen) as a template and using primers of SEQ ID NO: 26 and SEQ ID NO: 27, and the resulting PCR fragment was digested with XhoI and BamHI, ligated to the pGEM-PDCp-Gal10t that is digested with the same enzymes, producing pGEM-PDCp-NPT-Gal10t. FIG. 3 is a schematic view of a pGEM-PDCp-Gal10t vector. The pGEM-PDCp-NPT-Gal10t vector is an NPT overexpression deletion vector that is used as a template in preparation of a cassette for deletion of PDC1.

PCR was performed with pGEM-PDCp-NPT-Gal10t as a template and using primers of SEQ ID NO: 28 and SEQ ID NO: 29 to produce a PDC1 gene deletion cassette.

(3.2) Preparation of PDC1 Gene Deletion Cassette

Figure 4:
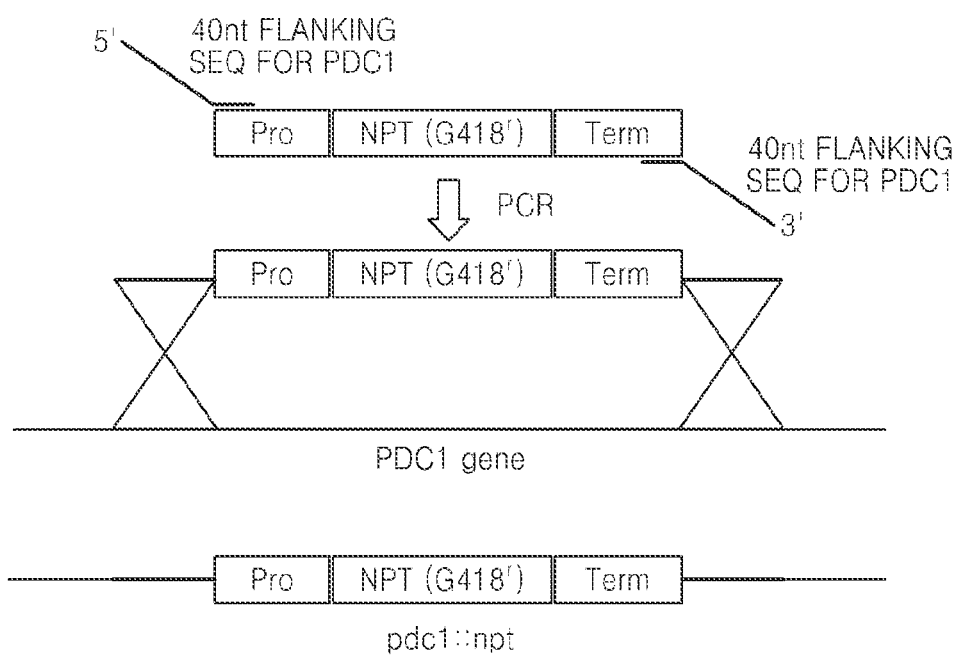
FIG. 4 illustrates a process of preparing a mutant strain by deleting PDC1 from a mother strain, *Saccharomyces cerevisiae* CEN.PK2-1D.
Figure 5:
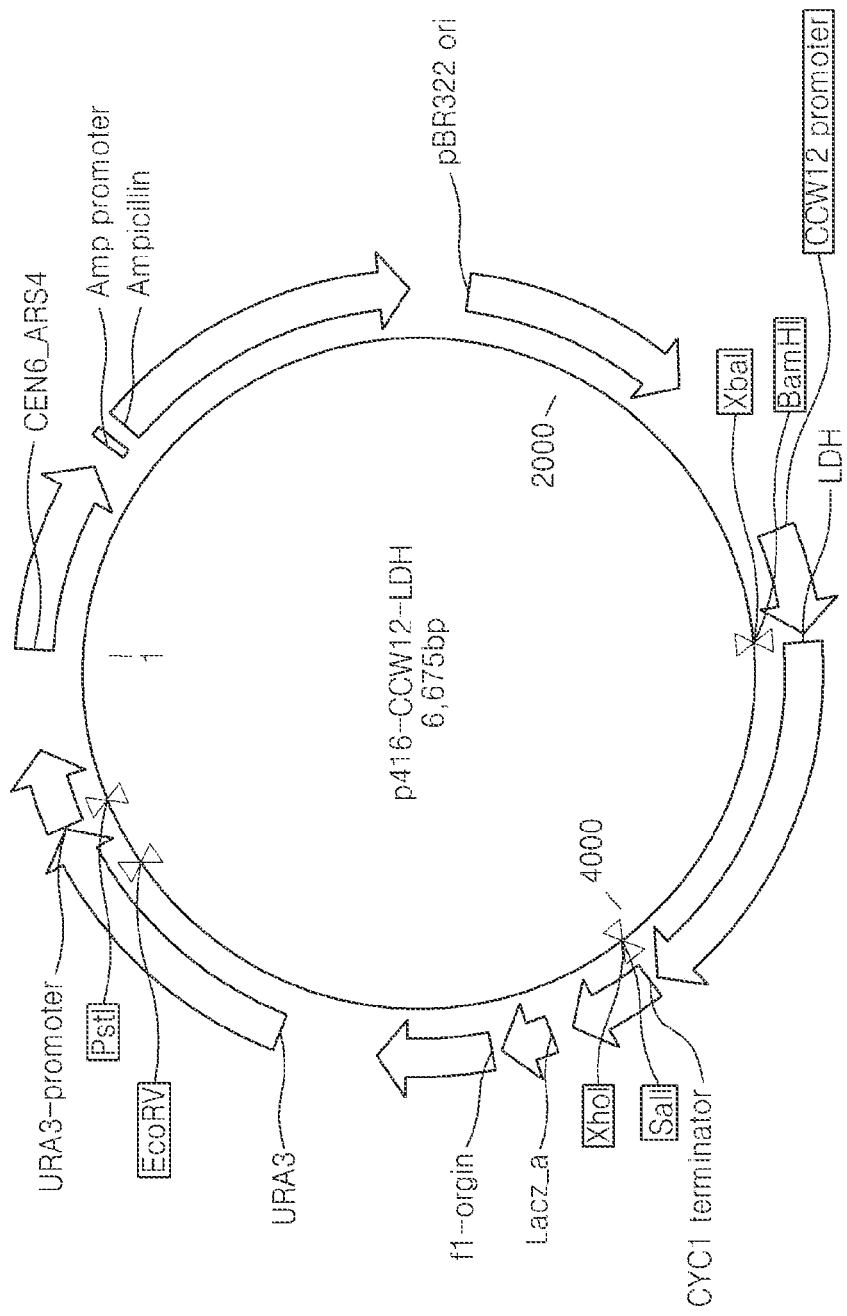
FIG. 5 is a schematic of a p416-CCW12-LDH vector.

A mutant strain, i.e. PDC1 deleted *Saccharomyces cerevisiae*, was prepared as follows. FIG. 4 illustrates a process of preparing the mutant strain by deleting PDC1 from a mother strain, *Saccharomyces cerevisiae* CEN.PK2-1D. *Saccharomyces cerevisiae* CEN.PK2-1D was spread on a YPD plate (including 10 g of yeast extract, 20 g of peptone, and 20 g of glucose) and incubated for 24 hours at 30□, and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and incubated in an incubator at a rate of about 230 rpm and at 30□. After about 4 to 5 hours, when the OD$_{600}$ reached about 0.5, the culture was centrifuged at a rate of about 4,500 rpm for about 10 minutes to harvest cells, and the cells were resuspensed in a lithium acetate solution at a concentration of about 100 mM. Then, the cells were harvested by performing centrifugation at a rate of about 4,500 rpm for about 10 minutes, resuspensed in a lithium acetate solution at a concentration of about 1 M including about 15% of glycerol, and then divided into a volume of about 100 ul each.

In order to delete PDC1, the PDC1 gene deletion cassette prepared in Example 2 was mixed with 50% of polyethylene glycol and a single stranded carrier DNA and reacted in a water bath for about 1 hour at 42° C., and then, the culture solution was spread on a YPD plate including about 100 ug/ml of geneticin and grown for about 24 hours or more at 30° C. Eight colonies (mutant strains) grown on the plate were selected, patched onto the fresh YPD plate including about 100 ug/ml of geneticin. At the same time, the selected colonies were inoculated into a YPD liquid medium with the same components as the YPD plate to isolate the genomic DNA from the above mutant strains by using a commonly used kit (Gentra Puregene Cell kit, Qiagen, USA). In order to confirm deletion of PDC1 by using the isolated genomic DNA as a template, PCR was performed by using primers of SEQ ID NOS: 30 and 31, and then, electrophoresis was performed on the obtained PCR product to confirm deletion of PDC1. As a result, *Saccharomyces cerevisiae* CEN.PK2-1D (ΔPDC1) was obtained.

(3.3) Preparation of *Saccharomyces cerevisiae* Strain in which PDC1 is Deleted and ADH6 is Overexpressed In order to insert the p416-PDCp-ADH6 plasmid prepared in Example 1 to *Saccharomyces cerevisiae* CEN.PK2-1D (ΔPDC1), the p416-PDCp-ADH6 plasmid was introduced in the same manner used in Example 2, and the introduction of the plasmid was confirmed. The obtained strain was named CEN.PK2-1D (ΔPDC1+ADH6).

Example 4

Preparation of Strain for High Efficient Production of Lactate and Introduction of ADH6 Overexpression Vector to the Prepared Strain In order to insert the p416-PDCp-ADH6 plasmid prepared in Example 1 to the prepared *Saccharomyces cerevisiae* CEN.PK2-1D (Δpdc1:PsIdhΔcyb2:PsIdhΔgpd1:PsIdh) (Accession Number: KCTC12415BP), a process was performed as follows. KCTC12415BP is a strain in which PDC1, CYB2, and GPD1 genes are deleted by introducing a L-Idh (PsLDH) gene derived from *Pelodiscus sinensis japonicus* at positions of PDC1, CYB2, and GPD1 genes in *Saccharomyces cerevisiae* CEN.PK2-1D by homogenous recombination.

The p416-PDCp-ADH6 plasmid prepared in Example 1 was mixed with 50% of polyethylene glycol and a single stranded carrier DNA and reacted in a water bath for about 1 hour at 42° C., and then, the culture solution was spread on a uracil-free minimal agar plate (including YSD, 6.7 g/L yeast nitrogen base without amino acids, 1.4 g/L Amino acid dropout mix (-ura)) and grown for about 24 hours or more at 30° C. Eight colonies (mutant strains) grown on the plate were selected, patched onto the fresh YSD (-ura) minimal agar plate, and at the same time, inoculated into a YSD (-ura) liquid medium to isolate the genomic DNA from the above mutant strains by using a commonly used kit (Yeast plasmid isolation kit, Clontech). In order to confirm the plasmid including ADH6, PCR was performed with the isolated plasmid DNA as a template and using primers of SEQ ID NOS: 20 and 21, and then, electrophoresis was performed on the obtained PCR product to confirm that the inserted plasmid is p416-PDCp-ADH6. As a result, *Saccharomyces cerevisiae* CEN.PK2-1D (Δpdc1:PsIdh Δcyb2:PsIdhΔgpdt: PsIdh+ADH6) was obtained, and the strain thus obtained was named KCTC12415BP(ADH6).

Example 5

Analysis of ADH6 Overexpression Effect to Each of Wild-Type *Saccharomyces cerevisiae* CEN.PK2-1D Strain and PDC1-Deleted *Saccharomyces cerevisiae* Strain The CEN.PK2-1D, CEN.PK2-1D(ADH6), CEN.PK2-1D (ΔPDC1), and CEN.PK2-1D (ΔPDC1+ADH6) strains prepared in Examples 2 and 3 were each spread on a YSD (-ura) agar plate and incubated for 24 hours or more at 30□, and then, a colony obtained therefrom was inoculated in about 50 ml of a YPD (-ura) including 40 g/L of glucose, and incubated in an aerobic condition for about 16 hours at 30° C. Fermentation was performed by measuring an amount of a cell concentration when an optical density at 600 nm ($OD_{600}$) reached 4.0 or greater by using a spectrophotometer in each of the 50 ml cultures of CEN.PK2-1D(ADH6), CEN.PK2-1D (ΔPDC1), and CEN.PK2-1D (ΔPDC1+ADH6), discarding the supernatant thereof after performing centrifuge, resuspending the cells, and inoculating again in 50 ml of a fresh YSD (-ura) including glucose. The cells were fermented in a stirring incubator maintaining 90 rpm for 16 hours at 30° C. During the fermentation, a sample was periodically obtained from the flask, and the obtained sample was centrifuged at 13,000 rpm for 10 minutes, and concentrations of glucose, glycerol, and ethanol, which are metabolic products, in the supernatant were analyzed by using an HPLC. An initial amount of glucose was 72 g/L.

As shown in Table 1, ADH6-overexpressed *Saccharomyces cerevisiae* CEN.PK2-1D (ADH6) strain had a smaller amount of ethanol production and a smaller amount of glucose consumption than those of the wild-type *Saccharomyces cerevisiae* CEN.PK2-1D.

Also, the ADH6-overexpressed *Saccharomyces cerevisiae* CEN.PK2-1D (ΔPDC1+ADH6) strain had a smaller amount of ethanol production and a smaller amount of glucose consumption than those of the *Saccharomyces cerevisiae* CEN.PK2-1D (ΔPDC1) strain.

It was confirmed that the ADH6-overexpressed *Saccharomyces cerevisiae* produced a smaller amount of glucose consumption but a similar amount of glycerol production compared to those of a strain that is not ADH6-overexpressed. Thus, it was confirmed that carbon flux in an ADH6-overexpressed strain changed by the overexpression of ADH6.

TABLE 1

| Strain | O.D. | Remaining glucose (g/L) | Glycerol (g/L) | Ethanol (g/L)) |
|---|---|---|---|---|
| CEN.PK2-1D | 12.19 ± 0.60 | 9.21 ± 0.71 | 1.61 ± 0.02 | 30.13 ± 0.33 |
| CEN.PK2-1D (ADH6) | 11.34 ± 0.18 | 13.1 ± 0.75 | 1.77 ± 0.06 | 28.11 ± 0.38 |
| CEN.PK2-1D (Δ PDC1) | 12.19 ± 0.60 | 7.08 ± 1.50 | 1.68 ± 0.01 | 31.20 ± 0.75 |
| CEN.PK2-1D (Δ PDC1 + ADH6) | 10.41 ± 0.02 | 24.26 ± 0.94 | 1.56 ± 0.02 | 22.25 ± 0.45 |

Example 6

Analysis of ADH6 Overexpression Effect to ADH6-Introduced *Saccharomyces cerevisiae* Strain A strain KCTC12415BP as a control group and the *Saccharomyces cerevisiae* KCTC12415BP (ADH6) strain prepared in Example 4 were each spread on a YSD (-ura) agar plate and incubated for 24 hours or more at 30° C., and then, a colony obtained therefrom was inoculated in about 50 ml of a YPD (-ura) including 40 g/L of glucose, and incubated in an aerobic condition for about 16 hours at 30° C.

Fermentation was performed by measuring an amount of a cell concentration when an optical density at 600 nm ($OD_{600}$) reached 4.0 or greater by using a spectrophotometer in each of the 50 ml cultures of KCTC12415BP and KCTC12415BP(ADH6), discarding the supernatant thereof after performing centrifuge, resuspending the cells, and inoculating again in 50 ml of a fresh YSD (-ura) including glucose. The cells were fermented in a stirring incubator maintaining 90 rpm for 16 hours at 30° C. During the fermentation, a sample was periodically obtained from the flask, and the obtained sample was centrifuged at 13,000 rpm for 10 minutes, and concentrations of glucose, lactate, glycerol, and ethanol, which are metabolic products, in the supernatant were analyzed by using an HPLC.

As shown in Table 2, an amount of ethanol production of *Saccharomyces cerevisiae* KCTC12415BP(ADH6), which is an ADH6-overexpression strain, was about 9.45 g/L, and this was smaller than that of *Saccharomyces cerevisiae* KCTC12415BP.

Also, an amount of glucose consumption of *Saccharomyces cerevisiae* KCTC12415BP(ADH6) was smaller than that of *Saccharomyces cerevisiae* KCTC12415BP. A lactate yield per glucose of the KCTC12415BP(ADH6) was about 49.47%, and this was about 10% increased amount compared to about 38.19% of yield of the control group, KCTC12415BP. Thus, it may be confirmed that the changed carbon flux in the ADH6-overexpression strain improved the lactate yield by the overexpression of ADH6.

TABLE 2

| Strain | O.D. | Lactate yield per glucose (%, g/g) | Remaining glucose (g/L) | Lactate (g/L) | Glycerol (g/L) | Ethanol (g/L)) |
|---|---|---|---|---|---|---|
| KCTC12415BP | 8.56 ± 0.46 | 38.19 ± 0.62 | 2.48 ± 1.24 | 25.02 ± 0.07 | 0 | 20.92 ± 0.50 |
| KCTC12415BP (ADH6) | 7.48 ± 0.06 | 49.47 ± 0.04 | 29.33 ± 0.14 | 19.13 ± 0.09 | 0 | 9.45 ± 0.01 |

Example 7

Analysis of ADH6 Overexpression Effect to ADH6-Introduced *Saccharomyces cerevisiae* CEN.PK2-1D (ΔPdc1:PsIdhΔCyb2:PsIdhΔGpd1:PsIdh) Strain A strain KCTC12415BP as a control group and the *Saccharomyces cerevisiae* KCTC12415BP (ADH6) strain prepared in Example 4 were each spread on a YPD agar plate and incubated for 24 hours or more at 30° C., and then, a colony obtained therefrom was inoculated in about 100 ml of a YPD including 80 g/L of glucose, and incubated in an aerobic condition for about 16 hours at 30° C.

Fermentation was performed by separately inoculating 100 ml of the culture of the KCTC12415BP and KCTC12415BP(ADH6) strains into a bioreactor containing 1 L of a synthesis medium, and the fermentation condition included initially 60 g/L of glucose and 20 g/L of yeast extract at 30° C. During the fermentation, pH was maintained at pH 5 by using 5N Ca(OH)$_2$ up to 16 hours, pH 4.5 up to 24 hours, and pH 3.0 up to 60 hours, and a concentration of glucose was maintained at 20 g/L. Additional synthesis medium components included 50 g/L of K$_2$HPO$_4$, 10 g/L of MgSO$_4$, 0.1 g/L of tryptophan, and 0.1 g/L of histidine in addition to glucose.

Figure 6A:
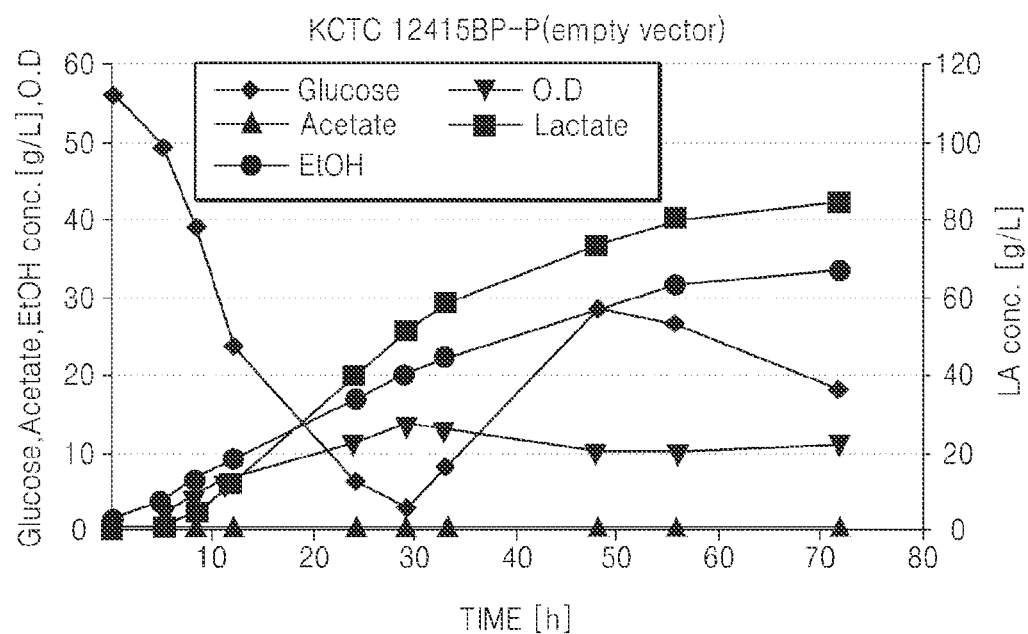
FIGS. 6A and 6B illustrate culturing characteristics KCTC12415BP and a mutant strain KCTC12415BP+ADH6 under culture conditions.
Figure 6B:
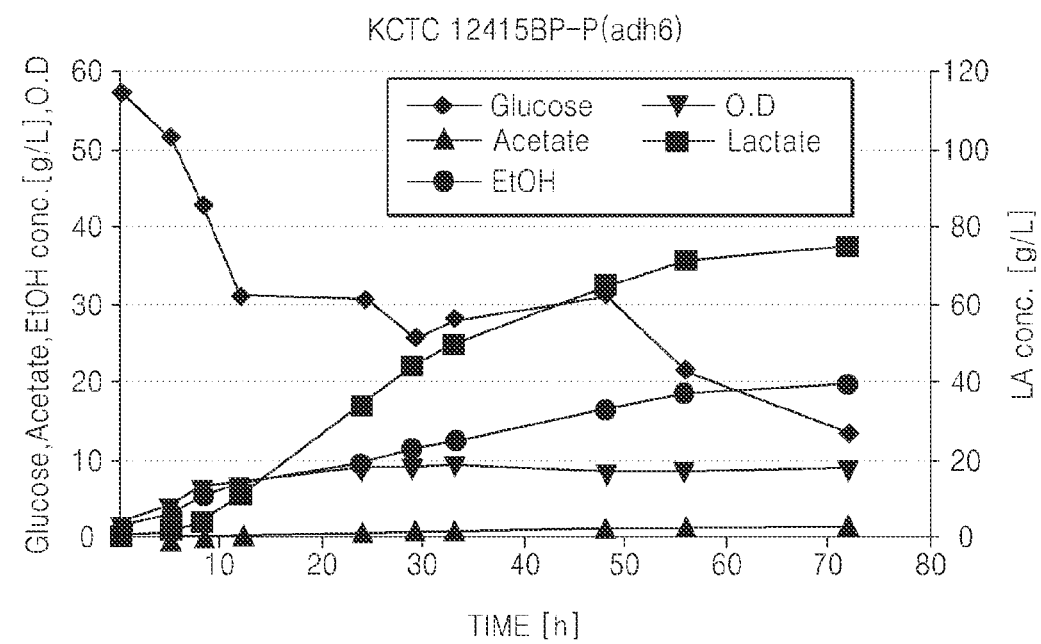
Figure 7:
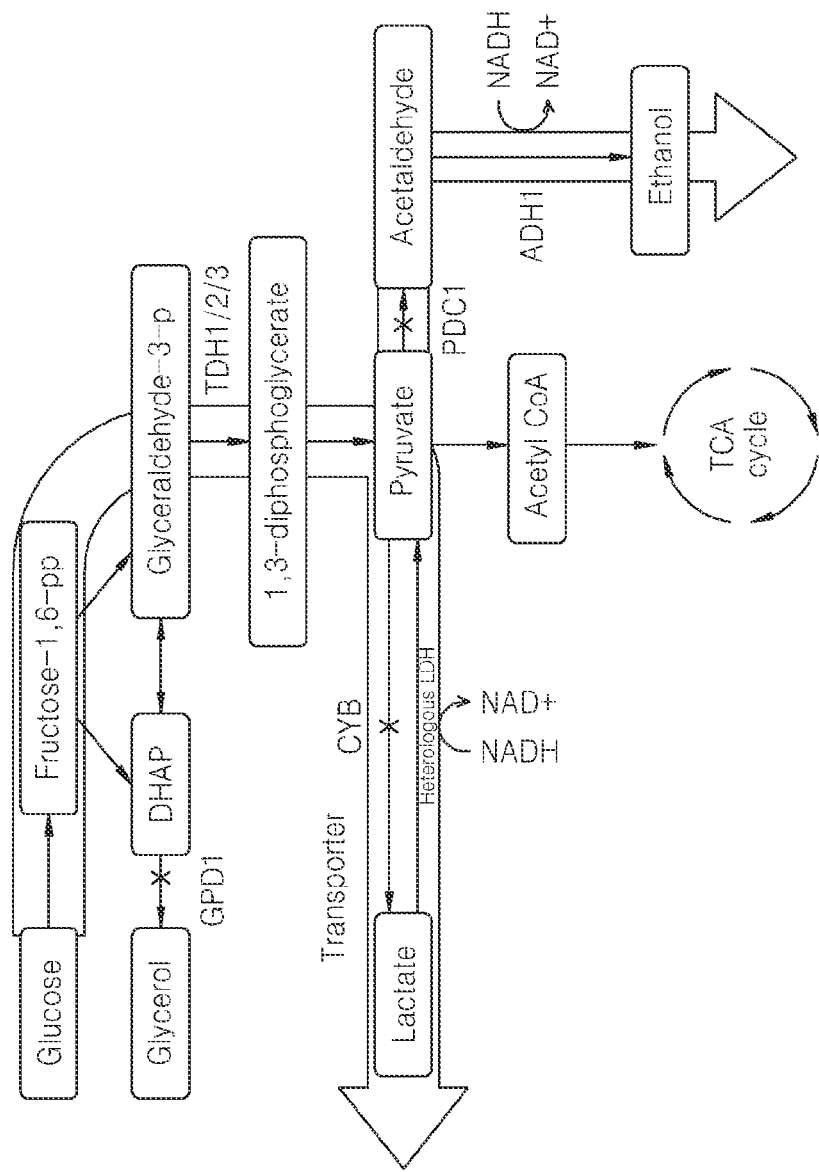
FIG. 7 is a schematic depicting pathways of producing ethanol and lactate of the KCTC12415BP strain.

A cell concentration in the culture was estimated by using a spectrophotometer, samples were periodically obtained from the bioreactor during the fermentation, the samples thus obtained were centrifuged at 13,000 rpm for 10 minutes, and then metabolic products and concentration s of lactate and glucose of the supernatants were analyzed by high pressure liquid chromatography (HPLC). FIGS. 6A and 6B show culture characteristics of KCTC12415BP and the mutant strain, KCTC12415BP(ADH6), under the fermentation condition. As shown in FIGS. 6A and 6B, the mutant strain, KCTC12415BP(ADH6), has a reduced ethanol productivity and have a high lactate yield as the strain consumes less glucose and produces lactate between 10 hours to 50 hours after starting the culturing.

[Accession Number]
Research Center Name: Korean Collection for Type Cultures (KCTC)

Accession Number: KCTC 12415BP

Accession Date: May 30, 2013

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant yeast cell comprising:
   a genetic modification that increases alcohol dehydrogenase 6 (ADH6) enzyme activity, wherein the genetic modification comprises:
   a genetic modification of a regulatory sequence of a gene encoding ADH6,
   an increase in the copy number of a gene encoding ADH6,
   or a combination thereof;
   and
   a genetic modification that decreases alcohol dehydrogenase 1 (ADH1) activity.

2. The recombinant yeast cell of claim 1, comprising an increase in the copy number of a gene encoding ADH6.

3. The recombinant yeast cell of claim 1, wherein the alcohol dehydrogenase 6 has an amino acid sequence comprising SEQ ID NO: 1.

4. The recombinant yeast cell of claim 2, wherein the gene encoding alcohol dehydrogenase 6 has a nucleotide sequence of SEQ ID NO: 2.

5. The recombinant yeast cell of claim 1, wherein the recombinant yeast cell further comprises a genetic modification that decreases pyruvate decarboxylase (PDC) activity.

6. The recombinant yeast cell of claim 5, wherein the genetic modification is deletion or inactivation of a PDC gene.

7. The recombinant yeast cell of claim 5, wherein the PDC enzyme has an amino acid sequence comprising SEQ ID NO: 3.

8. The recombinant yeast cell of claim 5, further comprising a genetic modification that reduces the activity of lactate cytochrome-c oxydoreductase (Cyb2), a genetic modification that reduces the activity of cytosolic glycerol-3-phosphate dehydrogenase (Gpd1), or a combination thereof.

9. The recombinant yeast cell of claim 8, wherein the recombinant yeast cell comprises deletion or inactivation of a gene that encodes Cyb2, Gpd1, or combination thereof.

10. The recombinant yeast cell of claim 8, wherein the Cyb2 has an amino acid sequence comprising SEQ ID NO: 5, and the Gpd1 has an amino acid sequence comprising SEQ ID NO: 7.

11. The recombinant yeast cell of claim 8, wherein a gene that encodes Cyb2 has a nucleotide sequence comprising SEQ ID NO: 6, and a gene that encodes Gpd1 has a nucleotide sequence comprising ef SEQ ID NO: 8.

12. The recombinant yeast cell of claim 1, comprising a genetic modification that increases activity of lactate dehydrogenase (LDH).

13. The recombinant yeast cell of claim 12, wherein the recombinant yeast cell comprises an exogenous gene encoding LDH.

14. The recombinant yeast cell of claim 1, wherein the recombinant yeast cell comprises
   an heterologous gene encoding ADH6;
   inactivation or deletion of (a) a gene that encodes PDC 1, PDC2, or both, (b) a gene that encodes Cyb2, (c) a gene that encodes Gpd1, or (d) a combination thereof;
   and a heterologous gene that encodes LDH classified as EC 1.1.1.27 or EC 1.1.1.28.

15. The recombinant yeast cell of claim 1, wherein the recombinant yeast cell is *Saccharomyces* genus, *Kluyveromyces* genus, *Candida* genus, *Pichia* genus, *Issatchenkia* genus, *Debaryomyces* genus, *Zykosaccharomyces* genus, or *Saccharomycopsis* genus.

16. The recombinant yeast cell of claim 1, wherein the recombinant yeast cell is *Saccharomyces cerevisiae*.

17. A method of decreasing ethanol production in a yeast cell, the method comprising genetically modifying a yeast cell to increase alcohol dehydrogenase 6 (ADH6) expression, wherein the genetic modification comprises:
   a genetic modification of a regulatory sequence of a gene encoding ADH6,
   an increase in the copy number of a gene encoding ADH6, or a combination thereof;
   and
   genetically modifying the yeast cell to decrease alcohol dehydrogenase 1 (ADH1) activity.

18. A method of producing lactate, the method comprising:
   culturing the yeast cell of claim 12 in cell culture medium; whereby the yeast cell produces lactate; and
   collecting lactate from the cell culture medium.

* * * * *

SEQUENCE LISTING

<160> NUMBER OF SEQ ID NOS: 31

<210> SEQ ID NO 1
<211> LENGTH: 360
<212> TYPE: PRT
<213> ORGANISM: Saccharomyces cerevisiae

<400> SEQUENCE: 1

```
Met Ser Tyr Pro Glu Lys Phe Glu Gly Ile Ala Ile Gln Ser His Glu
  1               5                  10                  15

Asp Trp Lys Asn Pro Lys Lys Thr Lys Tyr Asp Pro Lys Pro Phe Tyr
             20                  25                  30

Asp His Asp Ile Asp Ile Lys Ile Glu Ala Cys Gly Val Cys Gly Ser
         35                  40                  45

Asp Ile His Cys Ala Ala Gly His Trp Gly Asn Met Lys Met Pro Leu
     50                  55                  60

Val Val Gly His Glu Ile Val Gly Lys Val Lys Leu Gly Pro Lys
 65                  70                  75                  80

Ser Asn Ser Gly Leu Lys Val Gly Gln Arg Val Gly Val Gly Ala Gln
                 85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360
```

<210> SEQ ID NO 2
<211> LENGTH: 1083
<212> TYPE: DNA
<213> ORGANISM: Saccharomyces cerevisiae

<400> SEQUENCE: 2

| | |
|---|---|
| atgtcttatc ctgagaaatt tgaaggtatc gctattcaat cacacgaaga ttggaaaaac | 60 |
| ccaaagaaga caaagtatga cccaaaacca ttttacgatc atgacattga cattaagatc | 120 |
| gaagcatgtg gtgtctgcgg tagtgatatt cattgtgcag ctggtcattg gggcaatatg | 180 |
| aagatgccgc tagtcgttgg tcatgaaatc gttggtaaag ttgtcaagct agggcccaag | 240 |
| tcaaacagtg ggttgaaagt cggtcaacgt gttggtgtag gtgctcaagt cttttcatgc | 300 |
| ttggaatgtg accgttgtaa gaatgataat gaaccatact gcaccaagtt tgttaccaca | 360 |
| tacagtcagc cttatgaaga cggctatgtg tcgcagggtg gctatgcaaa ctacgtcaga | 420 |
| gttcatgaac atttgtggt gcctatccca gagaatattc catcacattt ggctgctcca | 480 |
| ctattatgtg gtggtttgac tgtgtactct ccattggttc gtaacggttg cggtccaggt | 540 |
| aaaaagttg gtatagttgg tcttggtggt atcggcagta tgggtacatt gatttccaaa | 600 |
| gccatggggg cagagacgta tgttatttct cgttcttcga gaaaaagaga agatgcaatg | 660 |
| aagatgggcg ccgatcacta cattgctaca ttagaagaag gtgattgggg tgaaaagtac | 720 |
| tttgacacct tcgacctgat tgtagtctgt gcttcctccc ttaccgacat tgacttcaac | 780 |
| attatgccaa aggctatgaa ggttggtggt agaattgtct caatctctat accagaacaa | 840 |
| cacgaaatgt tatcgctaaa gccatatggc ttaaaggctg tctccatttc ttacagtgct | 900 |
| ttaggttcca tcaaagaatt gaaccaactc ttgaaattag tctctgaaaa agatatcaaa | 960 |
| atttgggtgg aaacattacc tgttggtgaa gccggcgtcc atgaagcctt cgaaaggatg | 1020 |
| gaaaagggtg acgttagata tagatttacc ttagtcggct acgacaaaga attttcagac | 1080 |
| tag | 1083 |

<210> SEQ ID NO 3
<211> LENGTH: 563
<212> TYPE: PRT
<213> ORGANISM: Saccharomyces cerevisiae

<400> SEQUENCE: 3

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
            85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr

```
            130                 135                 140
Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
                195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
                260                 265                 270

Lys Glu Ala Val Glu Ser Ala Asp Leu Ile Leu Ser Val Gly Ala Leu
                275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Asn
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
                355                 360                 365

Trp Met Trp Asn Gln Leu Gly Asn Phe Leu Gln Glu Gly Asp Val Val
                370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
                515                 520                 525

Asp Asn Ser Lys Ile Arg Met Ile Glu Val Met Leu Pro Val Phe Asp
                530                 535                 540

Ala Pro Gln Asn Leu Val Glu Gln Ala Lys Leu Thr Ala Ala Thr Asn
545                 550                 555                 560
```

Ala Lys Gln

<210> SEQ ID NO 4
<211> LENGTH: 1692
<212> TYPE: DNA
<213> ORGANISM: Saccharomyces cerevisiae

<400> SEQUENCE: 4

```
atgtctgaaa ttactttggg taaatatttg ttcgaaagat taaagcaagt caacgttaac      60
accgttttcg gtttgccagg tgacttcaac ttgtccttgt ggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctcttctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact gaacgtccc agctaagttg     540
ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720
ccagctttcg tcaccccaat gggtaagggt tccattgacg aacaacaccc aagatacggt     780
ggtgtttacg tcggtaccct gtccaagcca gaagttaagg aagccgttga atctgctgac     840
ttgattttgt ctgtcggtgc ctttgttgtct gatttcaaca ccggttcttt ctcttactct     900
tacaagacca gaacattgt cgaattccac tccgaccaca tgaagatcag aaacgccact     960
ttcccaggtg tccaaatgaa attcgtttt g caaaagttgt tgaccaatat tgctgacgcc    1020
gctaagggtt acaagccagt tgctgtccca gctagaactc cagctaacgc tgctgtccca    1080
gcttctaccc cattgaagca agaatggatg tggaaccaat tgggtaactt cttgcaagaa    1140
ggtgatgttg tcattgctga aaccggtacc tccgctttcg gtatcaacca aaccactttc    1200
ccaaacaaca cctacggtat ctctcaagtc ttatggggtt ccattggttt caccactggt    1260
gctaccttgg gtgctgcttt cgctgctgaa gaaattgatc aaagaagag agttatctta    1320
ttcattggtg acggttcttt gcaattgact gttcaagaaa tctccaccat gatcagatgg    1380
ggcttgaagc catacttgtt cgtcttgaac aacgatggt acaccattga aaagttgatt    1440
cacggtccaa aggctcaata caacgaaatt caaggttggg accacctatc cttgttgcca    1500
actttcggtg ctaaggacta cgaaacccac agagtcgcta ccaccggtga atgggacaag    1560
ttgacccaag acaagtcttt caacgacaac tctaagatca gaatgattga ggttatgttg    1620
ccagtcttcg atgctccaca aaacttggtt gaacaagcta agttgactgc tgctaccaac    1680
gctaagcaat aa                                                         1692
```

<210> SEQ ID NO 5
<211> LENGTH: 591
<212> TYPE: PRT
<213> ORGANISM: Saccharomyces cerevisiae

<400> SEQUENCE: 5

```
Met Leu Lys Tyr Lys Pro Leu Leu Lys Ile Ser Lys Asn Cys Glu Ala
  1               5                  10                  15
```

```
Ala Ile Leu Arg Ala Ser Lys Thr Arg Leu Asn Thr Ile Arg Ala Tyr
         20                  25                  30

Gly Ser Thr Val Pro Lys Ser Lys Ser Phe Glu Gln Asp Ser Arg Lys
             35                  40                  45

Arg Thr Gln Ser Trp Thr Ala Leu Arg Val Gly Ala Ile Leu Ala Ala
 50                  55                  60

Thr Ser Ser Val Ala Tyr Leu Asn Trp His Asn Gly Gln Ile Asp Asn
 65                  70                  75                  80

Glu Pro Lys Leu Asp Met Asn Lys Gln Lys Ile Ser Pro Ala Glu Val
                 85                  90                  95

Ala Lys His Asn Lys Pro Asp Asp Cys Trp Val Val Ile Asn Gly Tyr
             100                 105                 110

Val Tyr Asp Leu Thr Arg Phe Leu Pro Asn His Pro Gly Gly Gln Asp
         115                 120                 125

Val Ile Lys Phe Asn Ala Gly Lys Asp Val Thr Ala Ile Phe Glu Pro
 130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                 165                 170                 175

Tyr Ala Pro Gly Glu Thr Lys Glu Asp Ile Ala Arg Lys Glu Gln Leu
             180                 185                 190

Lys Ser Leu Leu Pro Pro Leu Asp Asn Ile Ile Asn Leu Tyr Asp Phe
         195                 200                 205

Glu Tyr Leu Ala Ser Gln Thr Leu Thr Lys Gln Ala Trp Ala Tyr Tyr
 210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                 245                 250                 255

Val Asp Ile Ser Thr Asp Met Leu Gly Ser His Val Asp Val Pro Phe
             260                 265                 270

Tyr Val Ser Ala Thr Ala Leu Cys Lys Leu Gly Asn Pro Leu Glu Gly
         275                 280                 285

Glu Lys Asp Val Ala Arg Gly Cys Gly Gln Gly Val Thr Lys Val Pro
 290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                 325                 330                 335

Ser Asp Arg Lys Ile Thr Asp Asp Leu Val Lys Asn Val Glu Lys Leu
             340                 345                 350

Gly Val Lys Ala Leu Phe Val Thr Val Asp Ala Pro Ser Leu Gly Gln
         355                 360                 365

Arg Glu Lys Asp Met Lys Leu Lys Phe Ser Asn Thr Lys Ala Gly Pro
 370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                 405                 410                 415

Glu Leu Lys Lys Lys Thr Lys Leu Pro Ile Val Ile Lys Gly Val Gln
             420                 425                 430
```

Arg Thr Glu Asp Val Ile Lys Ala Ala Glu Ile Gly Val Ser Gly Val
            435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Val Arg Arg Gly Thr
                485                 490                 495

Asp Val Leu Lys Ala Leu Cys Leu Gly Ala Lys Gly Val Gly Leu Gly
                500                 505                 510

Arg Pro Phe Leu Tyr Ala Asn Ser Cys Tyr Gly Arg Asn Gly Val Glu
    515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
                580                 585                 590

<210> SEQ ID NO 6
<211> LENGTH: 1776
<212> TYPE: DNA
<213> ORGANISM: Saccharomyces cerevisiae

<400> SEQUENCE: 6

```
atgctaaaat acaaaccttt actaaaaatc tcgaagaact gtgaggctgc tatcctcaga      60
gcgtctaaga ctagattgaa cacaatccgc gcgtacggtt ctaccgttcc aaaatccaag     120
tcgttcgaac aagactcaag aaaacgcaca cagtcatgga ctgccttgag agtcggtgca     180
attctagccg ctactagttc cgtggcgtat ctaaactggc ataatggcca aatagacaac     240
gagccgaaac tggatatgaa taaacaaaag atttcgcccg ctgaagttgc caagcataac     300
aagcccgatg attgttgggt tgtgatcaat ggttacgtat acgacttaac gcgattccta     360
ccaaatcatc caggtgggca ggatgttatc aagtttaacg ccgggaaaga tgtcactgct     420
atttttgaac cactacatgc tcctaatgtc atcgataagt atatagctcc cgagaaaaaa     480
ttgggtcccc ttcaaggatc catgcctcct gaacttgtct gtcctcctta tgctcctggt     540
gaaactaagg aagatatcgc tagaaaagaa caactaaaat cgctgctacc tcctctagat     600
aatattatta acctttacga ctttgaatac ttggcctctc aaactttgac taaacaagcg     660
tgggcctact attcctccgg tgctaacgac gaagttactc acagagaaaa ccataatgct     720
tatcatagga ttttttttcaa accaaagatc cttgtagatg tacgcaaagt agacatttca     780
actgacatgt tgggttctca tgtggatgtt ccctttctacg tgtctgctac agctttgtgt     840
aaactgggaa accccttaga aggtgaaaaa gatgtcgcca gaggttgtgg ccaaggtgtg     900
acaaaagtcc cacaaatgat atctactttg gcttcatgtt cccctgagga aattattgaa     960
gcagcaccct ctgataaaca aattcaatgg taccaactat atgttaactc tgatagaaag    1020
atcactgatg atttggttaa aaatgtagaa aagctgggtg taaaggcatt atttgtcact    1080
gtggatgctc caagtttagg tcaaagagaa aagatatga agctgaaatt ttccaataca    1140
aaggctggtc caaaagcgat gaagaaaact aatgtagaag aatctcaagg tgcttcgaga    1200
gcgttatcaa agtttattga cccctctttg acttggaaag atatagaaga gttgaagaaa    1260
```

```
aagacaaaac tacctattgt tatcaaaggt gttcaacgta ccgaagatgt tatcaaagca    1320
gcagaaatcg gtgtaagtgg ggtggttcta tccaatcatg gtggtagaca attagatttt    1380
tcaagggctc ccattgaagt cctggctgaa accatgccaa tcctggaaca acgtaacttg    1440
aaggataagt tggaagtttt cgtggacggt ggtgttcgtc gtggtacaga tgtcttgaaa    1500
gcgttatgtc taggtgctaa aggtgttggt ttgggtagac cattcttgta tgcgaactca    1560
tgctatggtc gtaatggtgt tgaaaaagcc attgaaattt taagagatga aattgaaatg    1620
tctatgagac tattaggtgt tactagcatt gcggaattga agcctgatct tttagatcta    1680
tcaacactaa aggcaagaac agttggagta ccaaacgacg tgctgtataa tgaagtttat    1740
gagggaccta ctttaacaga atttgaggat gcatga                              1776
```

<210> SEQ ID NO 7
<211> LENGTH: 391
<212> TYPE: PRT
<213> ORGANISM: Saccharomyces cerevisiae

<400> SEQUENCE: 7

```
Met Ser Ala Ala Ala Asp Arg Leu Asn Leu Thr Ser Gly His Leu Asn
  1               5                  10                  15

Ala Gly Arg Lys Arg Ser Ser Ser Val Ser Leu Lys Ala Ala Glu
             20                  25                  30

Lys Pro Phe Lys Val Thr Val Ile Gly Ser Gly Asn Trp Gly Thr Thr
             35                  40                  45

Ile Ala Lys Val Val Ala Glu Asn Cys Lys Gly Tyr Pro Glu Val Phe
 50                  55                  60

Ala Pro Ile Val Gln Met Trp Val Phe Glu Glu Ile Asn Gly Glu
 65                  70                  75                  80

Lys Leu Thr Glu Ile Ile Asn Thr Arg His Gln Asn Val Lys Tyr Leu
             85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
        130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
            165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
            245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
```

|  | 275 |  |  | 280 |  |  | 285 |  |  |  |  |
|---|---|---|---|---|---|---|---|---|---|---|---|
| Glu | Glu | Thr | Tyr | Tyr | Gln | Glu | Ser | Ala | Gly | Val | Ala | Asp | Leu | Ile | Thr |
|  | 290 |  |  |  | 295 |  |  |  | 300 |  |  |

Thr Cys Ala Gly Gly Arg Asn Val Lys Val Ala Arg Leu Met Ala Thr
305                     310                     315                     320

Ser Gly Lys Asp Ala Trp Glu Cys Glu Lys Glu Leu Leu Asn Gly Gln
                325                     330                     335

Ser Ala Gln Gly Leu Ile Thr Cys Lys Glu Val His Glu Trp Leu Glu
        340                     345                     350

Thr Cys Gly Ser Val Glu Asp Phe Pro Leu Phe Glu Ala Val Tyr Gln
            355                     360                     365

Ile Val Tyr Asn Asn Tyr Pro Met Lys Asn Leu Pro Asp Met Ile Glu
        370                     375                     380

Glu Leu Asp Leu His Glu Asp
385                     390

```
<210> SEQ ID NO 8
<211> LENGTH: 1176
<212> TYPE: DNA
<213> ORGANISM: Saccharomyces cerevisiae

<400> SEQUENCE: 8
atgtctgctg ctgctgatag attaaactta acttccggcc acttgaatgc tggtagaaag      60
agaagttcct cttctgtttc tttgaaggct gccgaaaagc ctttcaaggt tactgtgatt     120
ggatctggta actggggtac tactattgcc aaggtggttg ccgaaaattg taagggatac     180
ccagaagttt cgctccaat agtacaaatg tgggtgttcg aagaagagat caatggtgaa      240
aaattgactg aaatcataaa tactagacat caaaacgtga atacttgcc tggcatcact      300
ctacccgaca atttggttgc taatccagac ttgattgatt cagtcaagga tgtcgacatc      360
atcgttttca acattccaca tcaattttg ccccgtatct gtagccaatt gaaaggtcat      420
gttgattcac acgtcagagc tatctcctgt ctaaagggtt ttgaagttgg tgctaaaggt      480
gtccaattgc tatcctctta catcactgag gaactaggta ttcaatgtgg tgctctatct      540
ggtgctaaca ttgccaccga gtcgctcaa gaacactggt ctgaaacaac agttgcttac      600
cacattccaa aggatttcag aggcgagggc aaggacgtcg accataaggt tctaaaggcc      660
ttgttccaca gaccttactt ccacgttagt gtcatcgaag atgttgctgg tatctccatc      720
tgtggtgctt tgaagaacgt tgttgcctta ggttgtggtt tcgtcgaagg tctaggctgg      780
ggtaacaacg cttctgctgc catccaaaga gtcggtttgg gtgagatcat cagattcggt      840
caaatgtttt tcccagaatc tagagaagaa acatactacc aagagtctgc tggtgttgct      900
gatttgatca ccacctgcgc tggtggtaga aacgtcaagg ttgctaggct aatggctact      960
tctggtaagg acgcctggga atgtgaaaag gagttgttga atggccaatc cgctcaaggt     1020
ttaattacct gcaaagaagt tcacgaatgg ttggaaacat gtggctctgt cgaagacttc     1080
ccattatttg aagccgtata ccaaatcgtt tacaacaact acccaatgaa gaacctgccg     1140
gacatgattg aagaattaga tctacatgaa gattag                                1176

<210> SEQ ID NO 9
<211> LENGTH: 289
<212> TYPE: DNA
<213> ORGANISM: Artificial Sequence
<220> FEATURE:
<223> OTHER INFORMATION: Synthetic (CYC promoter)
```

<400> SEQUENCE: 9

```
atttggcgag cgttggttgg tggatcaagc ccacgcgtag gcaatcctcg agcagatccg      60
ccaggcgtgt atatatagcg tggatggcca ggcaactta gtgctgacac atacaggcat     120
atatatatgt gtgcgacgac acatgatcat atggcatgca tgtgctctgt atgtatataa     180
aactcttgtt ttcttctttt ctctaaatat tctttcctta tacattagga cctttgcagc     240
ataaattact atacttctat agacacgcaa acacaaatac acacactaa                 289
```

<210> SEQ ID NO 10
<211> LENGTH: 401
<212> TYPE: DNA
<213> ORGANISM: Artificial Sequence
<220> FEATURE:
<223> OTHER INFORMATION: Synthetic (TEF promoter)

<400> SEQUENCE: 10

```
atagcttcaa aatgtttcta ctccttttt actcttccag attttctcgg actccgcgca      60
tcgccgtacc acttcaaaac acccaagcac agcatactaa atttcccctc tttcttcctc     120
tagggtgtcg ttaattaccc gtactaaagg tttggaaaag aaaaagaga ccgcctcgtt      180 tcttttctt cgtcgaaaaa ggcaataaaa atttttatca cgtttctttt tcttgaaaat      240 ttttttttg attttttct ctttcgatga cctcccattg atatttaagt taataaacgg       300
tcttcaattt ctcaagttc agtttcattt ttcttgttct attacaactt tttttacttc      360
ttgctcatta gaaagaaagc atagcaatct aatctaagtt t                         401
```

<210> SEQ ID NO 11
<211> LENGTH: 655
<212> TYPE: DNA
<213> ORGANISM: Artificial Sequence
<220> FEATURE:
<223> OTHER INFORMATION: Synthetic (GPD promoter)

<400> SEQUENCE: 11

```
agtttatcat tatcaatact cgccatttca agaatacgt aaataattaa tagtagtgat       60
tttcctaact ttatttagtc aaaaaattag ccttttaatt ctgctgtaac ccgtacatgc     120
ccaaaatagg gggcgggtta cacagaatat ataacatcgt aggtgtctgg gtgaacagtt     180
tattcctggc atccactaaa tataatgag cccgcttttt aagctggcat ccagaaaaaa      240
aaagaatccc agcaccaaaa tattgttttc ttcaccaacc atcagttcat aggtccattc     300
tcttagcgca actacagaga acaggggcac aaacaggcaa aaaacgggca caacctcaat     360
ggagtgatgc aacctgcctg gagtaaatga tgacacaagg caattgaccc acgcatgtat     420
ctatctcatt ttcttacacc ttctattacc ttctgctctc tctgatttgg aaaaagctga     480 aaaaaaggt tgaaaccagt tccctgaaat tattccccta cttgactaat aagtatataa      540
agacggtagg tattgattgt aattctgtaa atctatttct taaacttctt aaattctact     600
tttatagtta gtcttttttt tagttttaaa acaccagaac ttagtttcga cggat          655
```

<210> SEQ ID NO 12
<211> LENGTH: 1468
<212> TYPE: DNA
<213> ORGANISM: Artificial Sequence
<220> FEATURE:
<223> OTHER INFORMATION: Synthetic (ADH promoter)

<400> SEQUENCE: 12

```
gccgggatcg aagaaatgat ggtaaatgaa ataggaaatc aaggagcatg aaggcaaaag      60
```

-continued

```
acaaatataa gggtcgaacg aaaaataaag tgaaaagtgt tgatatgatg tatttggctt      120
tgcggcgccg aaaaacgag tttacgcaat tgcacaatca tgctgactct gtggcggacc       180
cgcgctcttg ccggcccggc gataacgctg ggcgtgaggc tgtgcccggc ggagttttttt    240 gcgcctgcat tttccaaggt ttaccctgcg ctaaggggcg agattggaga agcaataaga     300
atgccggttg gggttgcgat gatgacgacc acgacaactg gtgtcattat ttaagttgcc      360
gaaagaacct gagtgcattt gcaacatgag tatactagaa gaatgagcca agacttgcga      420
gacgcgagtt tgccggtggt gcgaacaata gagcgaccat gaccttgaag gtgagacgcg      480
cataaccgct agagtacttt gaagaggaaa cagcaatagg gttgctacca gtataaatag      540
acaggtacat acaacactgg aaatggttgt ctgtttgagt acgctttcaa ttcatttggg      600
tgtgcacttt attatgttac aatatggaag ggaactttac acttctccta tgcacatata     660
ttaattaaag tccaatgcta gtagagaagg ggggtaacac ccctccgcgc tcttttccga      720 ttttttttcta aaccgtggaa tatttcggat atccttttgt tgtttccggg tgtacaatat    780
ggacttcctc ttttctggca accaaaccca tacatcggga ttcctataat accttcgttg     840
gtctccctaa catgtaggtg gcggagggga gatatacaat agaacagata ccagacaaga     900
cataatgggc taaacaagac tacaccaatt acactgcctc attgatggtg gtacataacg      960
aactaatact gtagccctag acttgatagc catcatcata tcgaagtttc actaccctt     1020 ttccatttgc catctattga agtaataata ggcgcatgca acttctttc tttttttttc    1080 ttttctctct cccccgttgt tgtctcacca tatccgcaat gacaaaaaa tgatggaaga     1140 cactaaagga aaaattaac gacaaagaca gcaccaacag atgtcgttgt tccagagctg     1200
atgaggggta tctcgaagca cacgaaactt tttccttcct tcattcacgc acactactct    1260
ctaatgagca acggtatacg gccttccttc cagttacttg aatttgaaat aaaaaaaagt    1320
ttgctgtctt gctatcaagt ataaatagac ctgcaattat taatcttttg tttcctcgtc    1380
attgttctcg ttccctttct tccttgtttc tttttctgca caatatttca agctatacca    1440
agcatacaat caactccaag ctggccgc                                        1468
```

<210> SEQ ID NO 13
<211> LENGTH: 332
<212> TYPE: PRT
<213> ORGANISM: Pelodiscus sinensis japonicus

<400> SEQUENCE: 13

```
Met Ser Val Lys Glu Leu Leu Ile Gln Asn Val His Lys Glu His
  1               5                  10                  15

Ser His Ala His Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Arg Gly Glu Met Leu Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
```

|   |   |   | 115 |   |   |   | 120 |   |   |   | 125 |   |   |
|---|---|---|-----|---|---|---|-----|---|---|---|-----|---|---|

Pro Asp Cys Met Leu Leu Val Val Ser Asn Pro Val Asp Ile Leu Thr
130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
            165                 170                 175

Lys Leu Gly Ile His Ser Leu Ser Cys His Gly Trp Ile Ile Gly Glu
        180                 185                 190

His Gly Asp Ser Ser Val Pro Val Trp Ser Gly Val Asn Val Ala Gly
    195                 200                 205

Val Ser Leu Lys Ala Leu Tyr Pro Asp Leu Gly Thr Asp Ala Asp Lys
210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
            245                 250                 255

Ala Asp Leu Ala Glu Thr Val Met Lys Asn Leu Arg Arg Val His Pro
        260                 265                 270

Ile Ser Thr Met Val Lys Gly Met Tyr Gly Val Ser Ser Asp Val Phe
    275                 280                 285

Leu Ser Val Pro Cys Val Leu Gly Tyr Ala Gly Ile Thr Asp Val Val
290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
            325                 330

<210> SEQ ID NO 14
<211> LENGTH: 999
<212> TYPE: DNA
<213> ORGANISM: Pelodiscus sinensis japonicus

<400> SEQUENCE: 14
atgtccgtaa aggaactact tatacaaaac gtccataagg aggagcattc tcacgctcac      60
aataagataa cagttgtagg agtaggtgca gtaggtatgg catgtgctat ttcgatatta     120
atgaaagact tggctgatga actagccttg gttgatgtga ttgaggataa gttacgtgga     180
gaaatgttag atttgcaaca tggttcattg ttcttgagaa cccccaaaat tgtctcgggt     240
aaggattatt cagtcactgc tcattctaaa ctggttatca ttacagcagg tgcaagacag     300
caagaagggg agagcagact aaatctggtt caacgtaatg tcaacatctt caagtttatc     360
atcccgaacg tagtaaaata cagtccagac tgcatgttgc ttgttgtgag taatccagtt     420
gacatcttaa cctatgttgc gtggaaaatc agtgggtttc caaaacatag ggtgattggc     480
tcaggatgca accttgatag cgccaggttt aggtatctaa tgggagaaaa attaggtatt     540
cactccttat cttgtcatgg ctggataata ggcgaacatg gtgattcttc ggtacctgtt     600
tggtccgggg ttaatgtggc tggtgttagt ttaaaagcat tatatcctga cctgggtact     660
gatgccgata agaacattg gaagaagtg cacaaacaag tggttgattc tgcttacgaa      720
gttattaaac ttaagggcta cacttcttgg gctataggtc tatcagtagc tgatttggca     780
gaaaccgtta tgaaaaattt aagaagagtc cacccaattt ccacgatggt caagggtatg     840
tacggtgtta gctctgacgt cttcttatct gttccttgtg ttttgggata tgcgggaatt     900

```
acagacgtcg tgaagatgac attgaaatca gaggaagagg aaaaactaag aaagtcagcc    960
gatactctgt ggggcattca aaaggaattg cagttttaa                          999
```

<210> SEQ ID NO 15
<211> LENGTH: 252
<212> TYPE: DNA
<213> ORGANISM: Artificial Sequence
<220> FEATURE:
<223> OTHER INFORMATION: Synthetic (CYC1 terminator)

<400> SEQUENCE: 15

```
tcatgtaatt agttatgtca cgcttacatt cacgccctcc ccccacatcc gctctaaccg     60
aaaaggaagg agttagacaa cctgaagtct aggtccctat ttattttttt atagttatgt    120
tagtattaag aacgttattt atatttcaaa ttttctttt ttttctgtac agacgcgtgt     180
acgcatgtaa cattatactg aaaaccttgc ttgagaaggt tttgggacgc tcgaaggctt    240
taatttgcgg cc                                                       252
```

<210> SEQ ID NO 16
<211> LENGTH: 23
<212> TYPE: DNA
<213> ORGANISM: Artificial Sequence
<220> FEATURE:
<223> OTHER INFORMATION: Synthetic (forward primer)

<400> SEQUENCE: 16

```
gagctcaaca agctcatgca aag                                            23
```

<210> SEQ ID NO 17
<211> LENGTH: 21
<212> TYPE: DNA
<213> ORGANISM: Artificial Sequence
<220> FEATURE:
<223> OTHER INFORMATION: Synthetic (reverse primer)

<400> SEQUENCE: 17

```
tctagagatt tgactgtgtt a                                              21
```

<210> SEQ ID NO 18
<211> LENGTH: 32
<212> TYPE: DNA
<213> ORGANISM: Artificial Sequence
<220> FEATURE:
<223> OTHER INFORMATION: Synthetic (forward primer)

<400> SEQUENCE: 18

```
tctagaatgt cttatcctga gaaatttgaa gg                                  32
```

<210> SEQ ID NO 19
<211> LENGTH: 32
<212> TYPE: DNA
<213> ORGANISM: Artificial Sequence
<220> FEATURE:
<223> OTHER INFORMATION: Synthetic (reverse primer)

<400> SEQUENCE: 19

```
ctcgagctag tctgaaaatt ctttgtcgta gc                                  32
```

<210> SEQ ID NO 20
<211> LENGTH: 20
<212> TYPE: DNA
<213> ORGANISM: Artificial Sequence
<220> FEATURE:
<223> OTHER INFORMATION: Synthetic (forward primer)

```
<400> SEQUENCE: 20
aattaaccct cactaaaggg                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic (reverse primer)

<400> SEQUENCE: 21
caaattaaag ccttcgagcg                                              20

<210> SEQ ID NO 22
<211> LENGTH: 40
<212> TYPE: DNA
<213> ORGANISM: Artificial Sequence
<220> FEATURE:
<223> OTHER INFORMATION: Synthetic (forward primer)

<400> SEQUENCE: 22
gcggccgcga attcggatcc gtagatacat tgatgctatc                        40

<210> SEQ ID NO 23
<211> LENGTH: 29
<212> TYPE: DNA
<213> ORGANISM: Artificial Sequence
<220> FEATURE:
<223> OTHER INFORMATION: Synthetic (reverse primer)

<400> SEQUENCE: 23
gcggccgctc cgcggctcgt gctatattc                                    29

<210> SEQ ID NO 24
<211> LENGTH: 23
<212> TYPE: DNA
<213> ORGANISM: Artificial Sequence
<220> FEATURE:
<223> OTHER INFORMATION: Synthetic (forward primer)

<400> SEQUENCE: 24
gaattcaaca agctcatgca aag                                          23

<210> SEQ ID NO 25
<211> LENGTH: 27
<212> TYPE: DNA
<213> ORGANISM: Artificial Sequence
<220> FEATURE:
<223> OTHER INFORMATION: Synthetic (reverse primer)

<400> SEQUENCE: 25
gaattcctcg aggatttgac tgtgtta                                      27

<210> SEQ ID NO 26
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 26
ccgctcgaga tgattgaaca agatgg                                       26

<210> SEQ ID NO 27
```

```
<211> LENGTH: 27
<212> TYPE: DNA
<213> ORGANISM: Artificial Sequence
<220> FEATURE:
<223> OTHER INFORMATION: Synthetic (reverse primer)

<400> SEQUENCE: 27
cgcggatcct cagaagaact cgtcaag                                  27

<210> SEQ ID NO 28
<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 28
aagatctacg aagttgaagg tatgagatgg gctggtaacg taatacgact cactataggg    60

<210> SEQ ID NO 29
<211> LENGTH: 61
<212> TYPE: DNA
<213> ORGANISM: Artificial Sequence
<220> FEATURE:
<223> OTHER INFORMATION: Synthetic (reverse primer)

<400> SEQUENCE: 29
gcttccttaa cttctggctt ggacaaggta ccgacgtaaa acaagctca tgcaaagagg     60
t                                                                   61

<210> SEQ ID NO 30
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 30
gctcttctct accctgtcat tc                                       22

<210> SEQ ID NO 31
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 31
tagtgtacag ggtgtcgtat ct                                       22
```